(12) United States Patent
Rothmann et al.

(10) Patent No.: US 9,422,593 B2
(45) Date of Patent: Aug. 23, 2016

(54) METHODS AND COMPOSITIONS FOR SEQUENCE-SPECIFIC PURIFICATION AND MULTIPLEX ANALYSIS OF NUCLEIC ACIDS

(75) Inventors: Thomas Rothmann, Langenfeld (DE); Irina Nazarenko, Gaithersburg, MD (US); Dominic O'Neil, Hilden (DE); Arvind Virmani, Gaithersburg, MD (US); Brian Lowe, Olney, MD (US); Shiuli Agarwal, Somerville, MA (US); Holly Basham, Reisterstown, MD (US)

(73) Assignee: QIAGEN GAITHRESBURG, INC, Gaithersburg, MD (US)

( * ) Notice: Subject to any disclaimer, the term of this patent is extended or adjusted under 35 U.S.C. 154(b) by 46 days.

(21) Appl. No.: 13/110,660

(22) Filed: May 18, 2011

(65) Prior Publication Data

US 2012/0045756 A1 Feb. 23, 2012

Related U.S. Application Data

(60) Provisional application No. 61/346,218, filed on May 19, 2010.

(51) Int. Cl.
| | |
|---|---|
| *C12P 19/34* | (2006.01) |
| *C12Q 1/68* | (2006.01) |
| *C07H 21/02* | (2006.01) |
| *C07H 21/04* | (2006.01) |
| *C07H 21/00* | (2006.01) |

(52) U.S. Cl.
CPC .............. *C12Q 1/6806* (2013.01); *C12Q 1/689* (2013.01)

(58) Field of Classification Search
USPC ........... 435/6.1, 6.11, 6.12, 91.1, 91.2, 91.51; 436/94, 501, 544, 545, 546; 536/23.1, 536/24.3, 24.33, 25.3
See application file for complete search history.

(56) References Cited

U.S. PATENT DOCUMENTS

| 4,486,536 A | 12/1984 | Baker et al. |
|---|---|---|
| 4,486,539 A | 12/1984 | Ranki et al. |

(Continued)

FOREIGN PATENT DOCUMENTS

| EP | 0079139 | 5/1983 |
|---|---|---|
| EP | 0 163 220 | 12/1985 |

(Continued)

OTHER PUBLICATIONS

Rych et al., A computer program for choosing optimal oligonucleotides for filter hybridization, sequencing and in vitro amplification of DNA. Nucleic Acids Research, 17, 8543-8551, 1989.*

(Continued)

*Primary Examiner* — Frank Lu
(74) *Attorney, Agent, or Firm* — McBee Moore Vanik Woodward IP, LLC

(57) ABSTRACT

Methods and materials for determining the presence of at least one nucleic acid in a sample are provided, said methods comprising (1) a purification step using sequence specific hybrid capture; (2) an amplification step; and (3) a detection step comprising contacting the target nucleic acid with a plurality of detectably labeled nucleic acid detection probes, wherein each (a) bears a different detectable label from the other detection probes, and/or (b) has a different melting temperature from probes bearing the same detectable label. Also disclosed are compositions and kits for use in such a method.

24 Claims, 4 Drawing Sheets

(56) References Cited

U.S. PATENT DOCUMENTS

| | | |
|---|---|---|
| 4,563,417 A | 1/1986 | Alabrella et al. |
| 4,563,419 A | 1/1986 | Ranki et al. |
| 4,689,294 A | 8/1987 | Boguslawski et al. |
| 4,731,325 A | 3/1988 | Palva et al. |
| 4,732,847 A | 3/1988 | Stuart et al. |
| 4,743,535 A | 5/1988 | Carrico |
| 4,751,177 A | 6/1988 | Stabinsky et al. |
| 4,775,619 A | 10/1988 | Urdea |
| 4,833,084 A | 5/1989 | Carrico |
| 4,851,330 A | 7/1989 | Kohne et al. |
| 4,865,980 A | 9/1989 | Stuart et al. |
| 4,868,105 A | 9/1989 | Urdea et al. |
| 4,889,798 A | 12/1989 | Rabbani |
| 4,894,325 A | 1/1990 | Englehardt et al. |
| 5,082,830 A | 1/1992 | Brakel et al. |
| 5,106,727 A | 4/1992 | Hartley et al. |
| 5,116,734 A | 5/1992 | Higgs et al. |
| 5,200,313 A | 4/1993 | Carrico |
| 5,288,611 A | 2/1994 | Kohne et al. |
| 5,374,524 A | 12/1994 | Miller et al. |
| 5,424,413 A | 6/1995 | Hogan et al. |
| 5,437,977 A | 8/1995 | Segev |
| 5,474,895 A | 12/1995 | Ishii et al. |
| 5,484,699 A | 1/1996 | Bouma et al. |
| 5,545,806 A | 8/1996 | Lonberg et al. |
| 5,545,807 A | 8/1996 | Surani et al. |
| 5,556,748 A | 9/1996 | Douglas |
| 5,614,362 A | 3/1997 | Urdea et al. |
| 5,623,049 A | 4/1997 | Lobberding et al. |
| 5,627,030 A | 5/1997 | Pandian et al. |
| 5,629,153 A | 5/1997 | Urdea |
| 5,629,156 A | 5/1997 | Shah et al. |
| 5,635,352 A | 6/1997 | Urdea et al. |
| 5,641,630 A | 6/1997 | Snitman |
| 5,656,731 A | 8/1997 | Urdea |
| 5,681,697 A | 10/1997 | Urdea et al. |
| 5,681,897 A | 10/1997 | Silvis et al. |
| 5,695,926 A | 12/1997 | Cros et al. |
| 5,702,893 A | 12/1997 | Urdea et al. |
| 5,728,531 A | 3/1998 | Yamada et al. |
| 5,731,153 A | 3/1998 | Lucas et al. |
| 5,736,316 A | 4/1998 | Irvine et al. |
| 5,747,244 A | 5/1998 | Sheridan et al. |
| 5,747,248 A | 5/1998 | Collins |
| 5,750,338 A | 5/1998 | Collins et al. |
| 5,759,773 A | 6/1998 | Tyagi et al. |
| 5,786,183 A | 7/1998 | Ryder et al. |
| 5,792,606 A | 8/1998 | Deger et al. |
| 5,800,994 A | 9/1998 | Martinelli et al. |
| 5,814,492 A | 9/1998 | Carrino et al. |
| 5,821,339 A | 10/1998 | Schafer et al. |
| 5,827,661 A | 10/1998 | Blais |
| 5,853,993 A | 12/1998 | Dellinger et al. |
| 5,888,724 A | 3/1999 | Silverstein et al. |
| 5,981,179 A | 11/1999 | Lorincz et al. |
| 5,994,079 A | 11/1999 | De La Rosa et al. |
| 6,010,895 A | 1/2000 | Deacon et al. |
| 6,027,897 A | 2/2000 | Lorincz et al. |
| 6,043,038 A | 3/2000 | Sivaraja et al. |
| 6,057,099 A | 5/2000 | Nathan et al. |
| 6,083,925 A | 7/2000 | Li et al. |
| 6,110,676 A | 8/2000 | Coull et al. |
| 6,110,682 A | 8/2000 | Dellinger et al. |
| 6,110,687 A | 8/2000 | Nilsen |
| 6,207,385 B1 | 3/2001 | Stanley |
| 6,221,581 B1 | 4/2001 | Engelhardt et al. |
| 6,225,053 B1 | 5/2001 | Garcia et al. |
| 6,228,578 B1 | 5/2001 | Impraim et al. |
| 6,228,580 B1 | 5/2001 | Blumenfeld et al. |
| 6,232,462 B1 | 5/2001 | Collins et al. |
| 6,268,128 B1 | 7/2001 | Collins et al. |
| 6,277,579 B1 | 8/2001 | Lazar et al. |
| 6,280,954 B1 | 8/2001 | Ulfendahl |
| 6,326,136 B1 | 12/2001 | Lazar et al. |
| 6,355,424 B1 | 3/2002 | Lorincz et al. |
| 6,436,662 B1 | 8/2002 | Mielzynska et al. |
| 6,521,190 B1 | 2/2003 | Edens et al. |
| 6,544,732 B1 | 4/2003 | Chee et al. |
| 6,583,278 B1 | 6/2003 | Carter |
| 6,686,151 B1 | 2/2004 | Lazar et al. |
| 6,828,098 B2 | 12/2004 | Langmore et al. |
| 6,890,729 B2 | 5/2005 | Mielzynska et al. |
| 6,969,585 B2 | 11/2005 | Lorincz et al. |
| 6,977,148 B2 | 12/2005 | Dean et al. |
| 7,001,776 B2 | 2/2006 | Botacini Das Dores et al. |
| 7,371,518 B2 | 5/2008 | Lorincz et al. |
| 7,439,016 B1 | 10/2008 | Anthony et al. |
| 7,601,497 B2 | 10/2009 | Nazarenko et al. |
| 7,812,144 B2 | 10/2010 | Karlsen |
| 8,012,944 B2 | 9/2011 | Lacasse et al. |
| 2001/0055766 A1 | 12/2001 | Aristarkhov et al. |
| 2002/0012936 A1 | 1/2002 | Lorincz et al. |
| 2003/0096232 A1 | 5/2003 | Kris et al. |
| 2003/0108897 A1 | 6/2003 | Drmanac |
| 2003/0175765 A1 | 9/2003 | Kessler et al. |
| 2003/0175789 A1 | 9/2003 | Weininger et al. |
| 2004/0180362 A1 | 9/2004 | Lazar et al. |
| 2004/0214302 A1 | 10/2004 | Anthony et al. |
| 2005/0026976 A1 | 2/2005 | Curtin et al. |
| 2005/0032038 A1 | 2/2005 | Fisher et al. |
| 2005/0032105 A1 | 2/2005 | Bair et al. |
| 2005/0119217 A1 | 6/2005 | LaCasse et al. |
| 2005/0147996 A1 | 7/2005 | Sorge |
| 2006/0051809 A1 | 3/2006 | Nazarenko et al. |
| 2006/0160188 A1 | 7/2006 | Kurnit et al. |
| 2006/0240449 A1 | 10/2006 | McGlennen et al. |
| 2007/0109898 A1 | 5/2007 | Kasai |
| 2007/0154884 A1 | 7/2007 | Lorincz |
| 2007/0292899 A1 | 12/2007 | Lovell et al. |
| 2008/0200344 A1 | 8/2008 | Cheng |
| 2008/0247914 A1 | 10/2008 | Edens et al. |
| 2009/0032445 A1 | 2/2009 | Doak et al. |
| 2009/0263819 A1 | 10/2009 | Muraca |
| 2009/0286687 A1 | 11/2009 | Dressman et al. |
| 2009/0298187 A1 | 12/2009 | Nazarenko et al. |
| 2010/0081124 A1 | 4/2010 | Abravaya et al. |
| 2010/0105060 A1 | 4/2010 | Eder et al. |
| 2010/0126286 A1 | 5/2010 | Self et al. |
| 2010/0129789 A1 | 5/2010 | Self et al. |
| 2010/0159463 A1 | 6/2010 | Eder et al. |
| 2010/0311039 A1 | 12/2010 | Lowe et al. |
| 2011/0009277 A1 | 1/2011 | Devos et al. |
| 2014/0087449 A1 | 3/2014 | Ballhause et al. |

FOREIGN PATENT DOCUMENTS

| | | |
|---|---|---|
| EP | 0 167 366 | 1/1986 |
| EP | 0184017 | 6/1986 |
| EP | 0 281 927 | 9/1988 |
| EP | 0 288 737 | 11/1988 |
| EP | 0333465 | 9/1989 |
| EP | 0 336 454 | 11/1992 |
| EP | 0 144 914 | 6/1995 |
| EP | 0 415 978 | 3/1996 |
| EP | 0 703 296 | 3/1996 |
| EP | 1 806 410 A2 | 7/2007 |
| EP | 2 184 368 A1 | 5/2010 |
| JP | T H-07-505759 A | 6/1995 |
| JP | 2001157598 A | 6/2001 |
| JP | 200400508019 A | 3/2004 |
| JP | 2006-509500 A | 3/2006 |
| JP | 2006320334 A | 11/2006 |
| JP | T-2007-509861 A | 4/2007 |
| JP | 2008508901 A | 3/2008 |
| JP | 2009 106220 | 5/2009 |
| WO | 84/02721 | 7/1984 |
| WO | 8607387 | 12/1986 |
| WO | 88/03957 | 6/1988 |
| WO | 91/08312 | 6/1991 |
| WO | 93/10263 | 5/1993 |
| WO | 94/16108 | 7/1994 |
| WO | 95/16055 | 6/1995 |
| WO | 95/17430 | 6/1995 |
| WO | 96/40992 | 5/1996 |

(56) References Cited

FOREIGN PATENT DOCUMENTS

| | | |
|---|---|---|
| WO | 96/40992 | 12/1996 |
| WO | 97/05277 | 2/1997 |
| WO | 97/10364 | 3/1997 |
| WO | 97/31256 | 8/1997 |
| WO | 98/18488 | 5/1998 |
| WO | 98/22620 | 5/1998 |
| WO | 98/59044 | 12/1998 |
| WO | 99/02488 | 1/1999 |
| WO | 99/29909 | 6/1999 |
| WO | 99/32654 | 7/1999 |
| WO | 99/36571 | 7/1999 |
| WO | 99/39001 | 8/1999 |
| WO | 99/40224 | 8/1999 |
| WO | 99/49224 | 9/1999 |
| WO | 99/50459 | 10/1999 |
| WO | 00/60116 | 10/2000 |
| WO | 01/36681 | 5/2001 |
| WO | 01/96608 A1 | 12/2001 |
| WO | 0196608 | 12/2001 |
| WO | 02066993 A1 | 8/2002 |
| WO | 2004/046379 A1 | 6/2004 |
| WO | 2004/087950 | 10/2004 |
| WO | 2004087950 A2 | 10/2004 |
| WO | 2005042030 A1 | 5/2005 |
| WO | 2005/080602 | 9/2005 |
| WO | 2005/088311 A1 | 9/2005 |
| WO | 2006/020617 A1 | 2/2006 |
| WO | 2006039563 A2 | 4/2006 |
| WO | 2006/124771 A2 | 11/2006 |
| WO | 2007/056723 | 5/2007 |
| WO | 2007/130519 A2 | 11/2007 |
| WO | 2007134252 A1 | 11/2007 |
| WO | 2008/036061 | 3/2008 |
| WO | 2008/139938 A1 | 11/2008 |
| WO | 2008149237 A2 | 12/2008 |
| WO | 2009/057993 A1 | 5/2009 |
| WO | 2009/123996 | 10/2009 |
| WO | 2009/135832 A1 | 11/2009 |
| WO | 2010/004251 A1 | 1/2010 |
| WO | 2010/028382 | 3/2010 |
| WO | 2010/127228 A1 | 11/2010 |

OTHER PUBLICATIONS

International Preliminary Report on Patentability and Written Opinion Based on International Application No. PCT/US2011/037012 Mailed Nov. 29, 2012.
Yevgeniy S Belousov et al.: "Single nucleotide polymorphism genotyping by two colour melting curve analysis using the MGB elicpse TM probe system in challenging sequence environment" Human Genomics, Henry Stewart Publications, London, GB, vol. 1, No. 3, Jan. 1, 2004, pp. 209-217; XP001538494.
International Search Report and Written Opinion based on PCT/US2001/037012 mailed Apr. 17, 2012.
International Search Report and Written Opinion of PCT/US2011/22887, dated Jun. 1, 2011.
International Preliminary Report on Patentability and Written Opinion of PCT/US2009/062061, dated May 12, 2011.
International Preliminary Report on Patentability and Written Opinion of PCT/US2009/062041, dated May 12, 2011.
GenBank Submission FJ429103. 2009 [Retrieved from the Internet May 20, 2011: <URL:http://ncbl.nlm.nih.gov/nuccore/FJ429103.1>]; in entirety.
Zientara et al., 1998 "Use of reverse transcriptase-polymerase chain reaction (RT-PCR) and dot-blot hybridization for the detection and identification of African horse sickness virus nucleic acids" Arch. Virol 14:317-327.
Mansy et al., 1999 "A PCR Based DNA Hybridisation Capture System for the Detection of Human Cytomegalovirus. A Comparative Study with Other Identification Methods" Journal of Virological Methods 80:113-122.
Poulsen et al., 1999 "Detection of Clinical Vancomycin-Resistant Enterococci in Denmark by Multiplex PCR and Sandwich Hybridization" APMIS 107:404-12.

Sjoroos et al., 1998 "Time-Resolved Fluorometry Based Sandwich Hybridisation Assay for HLA-DQA1 Typing" Disease Markers 14:9-19.
Edman et al., 2000 "Pathogen Analysis and Genetic Predisposition Testing Using Microelectronic Arrays and Isothermal Amplification" Journal of Investigative Medicine, 48:93-101.
Monteiro et al.,1997 Evaluation of Performances of Three DNA Enzyme Immunoassays for Detection of Helicobacter pylori PCR Products from Biopsy Specimens Journal of Clinical Microbiology, 35;2931-2936.
Chiu et al., 1998 "Sandwich-type Deoxyribonucleic Acid Hybridization Assays Based on Enzyme Amplified Time-Resolved Fluorometry" Analyst, 123:1315-1319.
White et al., 1999 "Signal Amplification System for DNA Hybridization Assays Based on in vitro Expression of a DNA Label Encoding Apoaequorin" Nucleic Acids Research 27:i-viii.
Hakala et al., 1998 "Detection of Oligonucleotide Hybridization on a Single Microparticle by Time-Resolved Fluorometry: Quantitation and Optimization of a Sandwich Type Assay" Bioconjugate Chem. 9:316-321.
Zammatteo et al., 1997 "Comparison between Microwell and Bead Supports for the Detection of Human Cytomegalovirus Amplicons by Sandwich Hybridization" Analytical Biochemistry 253:180-189.
Fisher et al., 1997 "A System for the Quantitation of DNA Using a Microtiter Plate-Based Hybridization and Enzyme Amplification Technology" Analytical Biochemistry 251:280-287.
Wicks et al., 1998 "A Sandwich Hybridization Assay Employing Enzyme Amplification for Determination of Specific Ribosomal RNA from Unpurified Cell Lysates" Analytical Biochemistry 259:258-264.
Bruckner-Lea et al., 2000 "Rotating Rod Renewable Microcolumns for Automated, Solid-Phase DNA Hybridization Studies" Anal. Chem. 72:4135-4141.
Allen et al., 1998 "High Resolution Genetic Typing of the Class II HLA-DRB 1 Locus Using Group-Specific Amplification and SSO-Hybridisation in Microplates" Hereditas 129:161-167.
Alexandre et al., 1998 "Quantitative Determination of CMV DNA Using a Combination of Competitive PCR Amplification and Sandwich Hybridization" BioTechniques, 25: 676-683.
Hara et al., "Small Sample Whole-Genome Amplification," Optics East 2005, UCRL-PROC-216415, Lawrence Livermore National Laboratory, Oct. 21, 2005.
Brigotti, et al., "A rapid and sensitive method to measure the enzymatic activity of ribosome-inactivating proteins," Nucleic Acids Res., vol. 26, No. 18, pp. 4306-4307, 1998.
PCT/US2009/062061, International Searching Authority, Oct. 26, 2009 (6 pages).
PCT/US2009/062041, International Searching Authority, Oct. 26, 2009 (5 pages).
Bart "General Principles of Immunoprecipitation," Jul. 31, 2008 (XP002560372).
Bhan et al., "2',5'-Linked oligo-3'-deoxyribonucleoside phosphorothioate chimeras: thermal stability and antisense inhibition of gene expression," Nucleic Acids Research, 1997, vol. 25, No. 16, pp. 3310-3317 (XP-002560367).
Genetech Diagnostics Pvt. Ltd., "Digene HBV Test Hybrid Capture II," Jun. 6, 2008 (XP-002560368).
Hantz et al., "Evaluation of accuracy of three assays for human papillomavirus detection and typing: Hybrid Capture 2, HPV Consensus kit and Amplicor HPV," Pathologie Biologie, Feb. 2008, vol. 56, No. 1, pp. 29-35 (XP002560369).
Sandri et al., "Comparison of the Digene HC2 Assay and the Roche AMPLICOR Human Papillomavirus (HPV) Test for Detection of High-Risk HPV Genotypes in Cervical Samples," Journal of Clinical Microbiology, Jun. 2006, vol. 44, No. 6, pp. 2141-2146 (XP002560370).
Boston Bioproduct Inc., "Protein Extraction buffers," Sep. 2, 2007 (XP002560371).
Mittendorf T, et al., "HPV-DNA-Diagnostik zur Zervixkarzinomfrüherkennung: Deutsche Agentur für HTA des Deutschen Instituts für Medizinische Dokumentation und Information," 1. Auflage 2007.

(56) References Cited

OTHER PUBLICATIONS

Nanda K, et al., "Accuracy of the Papanicolaou Test in Screening for and Follow-up of Cervical Cytologic Abnormalities: A Systematic Review, Annals of Internal Medicine," 132(10):810-819, May 16, 2000.
Davey DD, et al., "Introduction and Commentary, Strategic Science Symposium, Human Papillomavirus Testing—Are you ready for a new era in cervical cancer screening?," Arch Pathol Lab Med, 127: 927-929, Aug. 2003.
Malloy C, et al., "HPV DNA Testing: Technical and Programmatic Issues for Cervical Cancer Prevention in Low-Resource Settings," Path, Dec. 2000.
Stacey SN, et al., "Translation of the Human Papillornavirus Type 16 E7 Oncoprotein from Bicistronic mRNA is independent of Splicing Events within the E6 Open Reading Frame," Journal of Virology. 69(11):7023-7031. Nov. 1995.
Hsu E, et al., Quantification of HPV-16 E6-E7 Transcription in Cervical Intraepithelial Neoplasia by Reverse Transcriptase Polymerase Chain Reaction, Int. J. Cancer: 55, 397-401 (1993).
Bohm S, et al., "The Predominant mRNA Class in HPV16-Infected Genital Neoplasias does not Encode the E6 or the E7 Protein," Int. J. Cancer: 55, 791-798 (1993).
Middleton, K, et al., "Organization of Human Papillomavirus Productive Cycle during Neoptastic Progression Provides a Basis for Selection of Diagnostic markers." Journal of Virology, Oct. 2003, pp. 10186-10201.
Kleter et al., "Development and clinical evaluation of a highly sensitive PCT-reverse hybridization line probe assay for detection and identification of anogenital human papillomafirus," In: Journal of clinical Micorbiology, Aug. 1991, vol. 37(8), pp. 2508-2517, see the whole document.
GenBank Accession No. AB027021, "Human papillomavirus type 82 DNA, complete genome.", Jun. 22, 2000. See http://ncbi.nlm.nih.gov/nuccor/6970427.
GenBank Accession No. X67161, "Human papillomavirus type L1 gene for major capsid protein.", Apr. 18, 2005. See http://ncbi.nlm.nih.gov/nuccore/1197494.
Park; JS, et al., "Physical Status and Expression of HPV Genes in Cervical Cancers," Gynec. Oncol. 95 (1997), pp. 121-129.
GenBank Accession No. U31794, "Human papillomavirus type 66, complete genome.", Oct. 18, 1995. See http://ncbi.nlm.nih.gov/nuccore/1020290.
Letter dated Jan. 6, 2010 to EPO re EP 1 038 022 (46 pages).
Letter to EPO dated Mar. 2, 209 re EP 1 038 022 (15 pages).
Letter to EPO dated Oct. 6, 2008 re EP 1 038 022 (27 pages).
Letter to EPO dated Aug. 8, 2008 re EP 1 038 022 (11 pages).
EPO decision dated May 27, 2008 re Opposition of EP 1 038 022 (19 pages).
Letter to EPO dated Jan. 25, 2008 re EP 1 038 022 (10 pages).
Letter to EPO dated Jan. 23, 2008 re EP 1 038 0E22 (6 pages).
Communication from EPO dated May 14, 2007 re EP 1 038 022 (8 pages).
Letter to EPO dated Oct. 4, 2006 re EP 1 038 022 (11 pages).
Letter to EPO dated Apr. 18, 2006 re EP 1 038 022 (10 pages).
Partial International Search Report for PCT/US2009/062041, mail date Jan. 5, 2010.
Partial International Search Report for PCT/US2009/062041, mail date Apr. 8, 2010.
Thai et al., "An HPV 16, 18, and 45 genotyping test based on Hybrid Capture technology," Journal of Clinical Virology 45, S1 (2009) pp. 593-597.
Kitagawa et al., "Comparison of Poly(A) Poly(dT) and Poly(I)) Poly(dC) as Immunogens for the Induction of Antibodies to RNA-DNA Hybrids," Molecular Immunology, vol. 19, No. 3, pp. 413-420, 1982.
Ishikawa et al., "Enzyme-Labeling of Antiboldies and Their Fragments for Enzyme Immunoassay and Immunohistochemical Staining," Journal of Immunoassay and Immunochemistry, 4: 3, 209-327.
Means et al., "Chemical Modifications of Proteins: History and Applications," Bioconjugate Chem. 1990, 1, 2-12.

Jakobovits et al., "Analysis of homozygous mutant chimeric mice: Deletion of the immunoglobulin heavy-chain joining region blocks B-cell development and antibody production," Proc. Natl. Acad. Sci. USA, vol. 90, pp. 2551-2555, Mar. 1993 Genetics.
Jakobovits et al., "Germ-line transmission and expression of a human-derived yeast artificial chromosome," pp. 255-258, Nature, vol. 362, Mar. 18, 1993.
International Search Report for PCT/US2009/041033, dated Dec. 22, 2009.
Sigurdsson et al "Human papillomavirus (HPV) in an icelandic population: the role of HPV DNA testing based on hybrid capture and PCR assays among women with screen-dtected abnormal PAP smears," In: International Journal of Cancer, Jul. 1997, vol. 72(3), pp. 446-452.
Michele De Villiers et al., "Classification of papillomarviruses," In: Virology, Jun. 2004, vol. 324(1), pp. 17-27—see table 3.
GenBank Accession No. K02718, "Human papillomavirus type 16 (HPV16), complete genome.", Mar. 18, 1994. See http://ncbi.nlm.nihgov/nuccore/333031.
GenBank Accession No. X74479, "human papillomavirus type 45 genomic DNA.", Apr. 18, 2005. See http://ncbi.nlm.nih.gov/nuccore/397022.
GenBank Accession No. X05015, "Human papillomavirus type 18 E6, E7, E1, E2, E4, E5, L1 & L2 genes.", Apr. 18, 2005. See http://ncbi.nlm.nih.gov/nuccore 60975.
GenBank Accession No. J04353, "Human papillomavirus type 31 (HPV-31), complete genome.". Mar. 18, 1994. See http://ncbi.nlm.nih.gov/nuccore/333048.
GenBank Accession No. M12732, "Human papillomavirus type 33, complete genome.", Mar. 21, 1994. See http://ncbi.nlm.nih.gov/nuccore/333049.
GenBank Accession No. M74117, "Human papiillomavirus type 35, complete genome.", May 10, 2002. See http://ncbi.nlm.nih.gov/nuccore/333050.
GenBank Accession No. M62849, "Human papillomavirus ORFs,", Jan. 26, 2001. See http://ncbi.nlm.nih.gov/nuccore/333245.
GenBank Accession No. M62877, "Human papillomavirus type 51 genomic DNA, partial sequence.", Oct. 29, 1999. See http://ncbi.nlm.nih.gov/nuccore/333087.
GenBank Accession No. X74481, "Human papillomavirus type 52 genomic DNA.", Apr. 18, 2005. See http://ncbi.nlm.nih.gov/nuccore/397038.
GenBank Accession No. X744133, "Human papillomavirus type 56 genomic DNA.", Apr. 18, 2005. See http://ncbi.nlm.nih.gov/nuccore/397053.
GenBank Accession No. D90400, "Human papillomavirus type 58, complete genome.", Dec. 7, 2007. See http://www.nlm.nih.gov/nuccore/222336.
GenBank Accession No. X77858, "Human papillomavirus type 59, complete viral genome.", Apr. 18, 2005. See http://ncbi.nlm.nih.gov/nuccore/557236.
Supplementary European Search Report of PCT/US2006/060603, dated Jul. 7, 2010 (8 pages).
Lowe, et al., "A computer program for selection of oligonucleotide primers for polymerase chain reactions", Nucleic Acid Res., vol. 18, No. 7, pp. 1757-1761 (1990).
International Search Report and Written Opinion of PCT/US2010/022264 dated Jun. 7, 2010 (19 pages).
Cohenford et al., "C-195, Rapid Detection of Chlamydia trachomatis from Specimens Collected from the ThinPrep Pap Test using Molecular Beacons and the Roche LightCycler," Abstracts of the General Meeting of the American Society for Microbiology, The Society, Washington, DC. (Jan. 1, 2001), p. 195, vol. 101, XP001098006.
Gentech Diagnostics: "Chlamydia DNA Test Kit," (Jun. 6, 2008), XP002578832, Retrieved from the Internet: URL: http://gentechin.com/chlamydiatestkit.htm.
Taha et al., "Universal Collection Medium (UCM) is as suitable as the Standard Transport Medium (STM) for Hybrid Capture II (HC-2) assay," Journal of Clinical Virology, (May 1, 2006), pp. 32-35, vol. 36, No. 1, XP005367693.
Darwin et al., "Comparison of Digene Hybrid Capture 2 and Conventional Culture for Detection of Chlamydia trachomatis and Neis-

(56) References Cited

OTHER PUBLICATIONS seria gonorrhoeae in Cervical Specimens," Journal of Clinical Microbiology, (Feb. 2002), pp. 641-644, vol. 40, No. 2, XP002578833.

Nazarenko et al., "A novel method of HPV genotyping using Hybrid Capture sample preparation method combined with GP5+/6+ PCR and multiplex detection on Luminex XMAP," Journal of Clinical Virology, (Dec. 1, 2008), pp. 76-81, vol. 154, No. 1-2, XP025680302.

International Search Report and Written Opinion of PCT/US10/33145, dated Aug. 5, 2010 (9 pages).

A Lorincz, "Hybrid Capture," Clin. Chem., (Jun. 1998), pp. 1363, vol. 44, No. 6. (Note that the page number of this literature listed on the ISR is incorrect).

Vernick et al., "The HPV DNA virus hybrid capture assay: What is it—and where do we go from here?" MLO Med. Lab. Obs., (Mar. 2003), pp. 8-10, 13, vol. 35, No. 3.

International Search Report and ritten Opinion of PCT/US2010/048714, dated Dec. 10, 2010 (14 pages).

International Preliminary Report on Patentability and Written Opinion of PCT/US2009/041033, dated Oct. 19, 2010 (6 pages).

International Search Report and Written Opinion of PCT/US2010/047769, dated Nov. 9, 2010 (11 pages).

Pachowics, et al., "Sequence specific large volume sample prep solution utilizing Hybrid Capture technology," 41st Annual Oak Ridge Conference; Baltimore, MD, Apr. 16, 2009; retrieved from the Internet: http://aacc.org/events/meeting_proceeding/2009/Docurnents/OakRidge09AllPosters.pdf.

Keegan et al., "Comparison of HPV detection technologies: Hybrid capture 2, PreTect HPV-Proofer and analysis of HPV DNA viral load in HPV16, HPV18 and HPV33 E6/E7 mRNA positive specimens," Journal of Virological Methods, Jan. 1, 2009, pp. 61-66, vol. 155, No. 1, Elsevier BV, XP025799776.

Murphy et al., "Isolation of RNA from cell lines and cervical cytology specimens stored in BD SurePath (TM) preservative fluid and downstream detection of housekeeping gene and HPV E6 expression using real time RT-PCR," Journal of Virological Methods, Mar. 1, 2009, pp. 138-144, vol. 156, No. 1-2, Elsevier BV, XP025941323.

Powell et al., "Recovery of human papillomavirus nucleic acids from liquid-based cytology media," Journal of Virological Methods, Oct. 1, 2006, pp. 58-62, vol. 137, No. 1, Elsevier BV, XP005600251.

Nindl et al., "Human Papillomavirus Distribution in Cervical Tissues of Different Morphology as Determined by Hybrid Capture Assay and PCR," International Journal of Gynecological Pathology, Jan. 1, 1997, pp. 197-204, vol, 16, No. 3, Lippincott-Raven Publishers, XP008011933.

Hernandez-Hernandez et al., "Association between high-risk human papillomavirus DNA load and precursor lesions of cervical cancer in Mexican women," Gynecologic Oncology, Aug. 2003, pp. 310-317, vol. 90, No. 2, Elsevier Science, XP002603500.

Tsai et al., "Association between Quantitative High-Risk Human Papillomavirus DNA Load and Cervical Intraepithelial Neoplasm Risk," Cancer Epidemiology, Biomarkers & Prevention: American Association for Cancer Research, Nov. 2005, pp. 2544-2549, vol. 14, No. 11 pt 1, XP002603501.

Moodley et al., "Human papillomavirus prevalence, viral load and pre-cancerous lesions of the cervix in women initiating highly active antiretroviral therapy in South Africa: a cross-sectional study," BMC Cancer, Aug. 7, 2009, pp. 1-8, vol. 9, No. 275, Biomed Central Ltd, XP002603502.

Ronco et al., "HPV triage for low grade (L-SIL) cytology is appropriate for women over 35 in mass cervical cancer screening using liquid based cytology," European Journal of Cancer, Feb. 1, 2007, pp. 476-480, vol. 43, No. 3, Pergamon Press, Oxford GB, XP005868775.

Lowe et al., "HPV Genotype Detection Using Hybrid Capture Sample Preparation Combined with Whole Genome Amplification and Multiplex Detection with Luminex XMAP," Journal of Molecular Diagnostics; Nov. 6, 2010; pp. 847-853; vol. 12; No. 6; American Society for Investigative Pathology.

Partial European Search Report of EP10185824; mailed Feb. 16, 2011 (8 pages).

Scott et al., "Detection of herpes simplex virus type 1 shedding in the oral cavity by polymerase chain reaction and enxyme-linked immunosorbent assay at the prodromal stage of recrudescent herpes labialis," Journal of Oral Pathology & Medicine; Aug. 1997; pp. 305-309; vol. 26; No. 7; XP009143938.

Ryncarz et al., "Development of a High-Throughput Quantitative Assay for Detecting Herpes Simplex Virus DNA in Clinical Samples," Journal of Clinical Microbiology; Jun. 1999; pp. 1941-1947; vol. 37, No. 6; American Society for Microbiology.

Broker et al., "A Molecular Portrait of Human Papillomavirus Carcinogenesis", Cancer Cells, vol. 7, pp. 197-208, 1989 (Roche EU Opposition).

Higgins et al., "Transcription Patterns of Human Papillomavirus Type 16 in Genital Intraepithelial Neoplasia: Evidence for Promoter Usage within the E7 Open Reading Frame during Epithelial Differentiation", Journal of General Virology, vol. 73, pp. 2047-2057, 1992 (Roche EU Opposition).

Karlsen et al., "Use of Multiple PCR Primer Sets for Optimal Detection of Human Papillomavirus", Journal of Clinical Microbiology, pp. 2095-2100, Sep. 1996 (Roche EU Opposition).

Park et al., "Physical Status and Expression of HPV Genes in Cervical Cancers", Gynecologic Oncology, vol. 65, pp. 121-129, 1997 (Roche EU Opposition).

Stoler et al., "Human Papillomavirus Type 16 and 18 Gene Expression in Cervical Neoplasias", Human Pathology, vol. 23, No. 2, pp. 117-128, Feb. 1992 (Roche EU Opposition).

De Villiers et al., "Classification of Papillomaviruses", Virology, vol. 324, pp, 17-27, 2004.

Howley et al., "A Rapid Method for Detecting and Mapping Homology between Heterologous DNAs", Journal of Biological Chemisny, vol. 254, No. 11, pp. 4879-4883, Jun. 10, 1979.

Law et al., "Conserved Polynucleotide Sequences Among the Genomics of Papillomaviruses", Journal of Virology, vol. 32, No. 1, pp. 199-207, Oct. 1979.

Heilman et al., "Cloning of Human Papilloma Virus Genomic DNAs and Analysis of Homologous Polynucleotide Sequences", Journal of Virology, vol. 36, No. 2, pp. 395-407, Nov. 1980.

Howard et al., "Optimizing the Hybrid Capture II Human Papillomavirus Test to Detect Cervical Intraepithelial Neoplasia", Obstetrics and Gynecology, vol. 100, No. 5, Part 1, pp. 972-980, Nov. 2002.

Lorincz, A.T., "Molecular Methods for the Detection of Human Papillomavirus Infection", Obstetrics and Gynecology Clinics of North America, vol. 23, No. 3, pp. 707-730, Sep. 1996.

Blair et al. "Herpes Simplex Virus Viron Stimulatory Protein mRNA Leader Contains Sequence Elements Which Increase Both Virus-Induced Transcription and tnRNA Stability." Journal of Virology, vol. 61, No. 8, pp. 2499-2508, Aug. 1987.

Larder et al. "Related Functional Domains in Virus DNA Polymerases,"The EMBO Journal. vol. 6, No. 1, pp. 160-175, 1987.

Chandler et al., Detection of Dengue-2 Viral RNA by Reversible Target Capture Flybridization., J. Clin. Microbiol., vol. 31 (10), pp. 2641-2647, 1993.

Mazzulli et al, 1999, Multicenter Comparison of the Digene Hybrid Capture CMV DNA Assay (version 2.0) the pp65 Antignenemia Assay, and Cell Culture for Detection of Cytomegalovirus Viremia, J Clin. Microbiol., vol. 37, No. 4, pp. 956-963, 1999.

Murakami et al., Fluorescent-Labeled Oligonucleotide Probes: Detection of Hybrid Formation in Solution by Fluorscence Polarization Spectroscopy, Nucleic Acids Res., vol. 19 (15), pp. 4097-4102, 1991.

Dunn and Hassell: "A Novel Method to Map Transcripts: Evidence for Homology between an Adenovirus niRNA and Discrete Multiple Regions of the Viral Genome" Cell, 12:23-36, Sep. 1977.

Coutlee et al., "Nonisotopic Detection of RNA in an Enzyme Imunoassay using a Monoclonal Antibody Against DNA-RNA Hybrids" Analytical Biochemistry 181:153-162, 1989.

Chen et al., "DNA Optical Sensor: A Rapid Method for the Detection of DNA Hybridization" Biosensors & Bioelectronics 13:451-458, 1998.

Chevrier et al., "Isolation of a Specific DNA fragment and Development of a PCR Based Method for the Detection of *Mycobacterium genavense*" FEMS Immunology and Medical Microbiology 23:243-452, 1999.

(56) References Cited

OTHER PUBLICATIONS

Hakala et al., "Simultaneous Detection of Several Oligonucleotides by Time-Resolved Fluorometry: The Use of a Mixture of Categorized Microparticles in a Sandwich Type Mixed-Phase Hybridization Assay" Nucleic Acid Research, 26:5581-5588, 1998.
Gelmetti et al., "Detection of Rabbit Haemorrhagic Disease Virus (RHDV) by In Situ Hybridisation With a Digoxigenin Labelled RNA Probe" Journal of Virological Methods 72:219-226, 1998.
Radtkey et al., "Rapid, High Fidelity Analysis of Simple Sequence Repeats on an Electronically Active DNA Microchip" Nucleic Acids Research 28:i-vi, 2000.
Namimatsu et al., "Detection of *Salmonella* by Using the Colorimetric DNA/rRNA Sandwich Hybridization in Microtiter Wells" J. Vet. Med. Sci. 62:615-619, 2000.
Lazar et al., 1999 "Hybrid Capture®: a Sensitive Signal Amplification-based Chemiluminescent Test for the Detection and Quantitation of Human Viral and Bacterial Pathogens".1. Clin. Ligand Assay 22:139-151.
Newman et al., 1989 "Solution Hybridization and Enzyme Immunoassay for Biotinylated DNA:RNA Hybrids to Detect Enteroviral RNA in Cell Culture" Mol. Cell Probes 3:375-382.
Lamoureux et al., 1997 "Detection of Campylobacter jejuni in Food and Poultry Viscera Using Immunomagnetic Separation and Microtitre Hybridization" J. Appl. Microbiol. 83:641-651.
Coutlee et al., 1990 "Quantitative Detection of Messenger RNA by Solution Hybridization and Enzyme Immunoassay" Biol. Chem. 265:11601-11604.
Stollar, B.D. and A. Rashtchian, 1987 "Immunochemical Approaches to Gene Probe Assays" Anal. Biochem. 161:387-394.
Blais, B.W., 1994 "Transcriptional Enhancement of the Listeria Monocytogenes PCR and Simple Immunoenzymatic Assay of the Product Using Anti-RNA:DNA Antibodies" Appl. Environ. Microbiol. 60:348-352.
Coutlee et al., 1991 "Detection of Transcripts of Human Papillomaviruses 16 and 18 in Cancer-derived Cell Lines and Cervical Biopsies by Enzyme Immunoassay for DNA-RNA Hybrids Following Solution Hybridization" J. Clin. Microbiol. 29:968-974.
Viscidi et al., 1989 "Monoclonal Antibody Solution Hybridization Assay for Detection of Human Immunodeficiency Virus Nucleic Acids" J. Clin. Microbiol. 27:120-125.
Boguslawski et al., 1986 "Characterization of Monoclonal Antibody to DNA:RNA and Its Application to Immunodetection of Hybrids" J. Immunol. Methods 89:123-130.
Coutlee et al., 1989 "Immunodetection of DNA with Biotinylated RNA Probes: A Study of Reactivity of a Monoclonal Antibody to DNA-RNA Hybrids" Anal. Biochem. 181:96-105.
Coutlee et al., 1991 "Immunodetection of DNA with Biotinylated RNA Probes: A Study of Reactivity of a Monoclonal Antibody to DNA-RNA Hybrids" Anal. Biochem. 198:217 (Published erratum).
Coutlee et al., 1989 "Comparison of Colorimetric Fluorescent, and Enzymatic Amplification Substrate Systems in an Enzyme immunoassay for Detection of DNA-RNA Hybrids" J. Clin. Microbiol. 27:1002-1007.
Dalrymple et al., DNA sequence of the herpes simplex virus type 1 gene whose product is responsible for transcriptional activation of immediate early promoters, Nucleic Acids Research, 1985, vol. 13, No. 21, pp. 7865-7879.
McLauchlan et al., DNA sequence homology between two co-linear loci on the HSV genome which have different transforming abilities, The EMBO Journal, 1983, vol. 2, No. 11, pp, 1953-1961.
Goldsborough et al., Nucleotide Sequence of Human Papillomavirus Type 31: A Cervical Neoplasia Associated Virus, Virology, 1989, vol. 171, pp. 306-311.
McGeoch et al., "DNA Sequence and Genetic Content of the HindIII 1 Region in the Short Unique Component of the Herpes Simplex Virus Type 2 Genome, Identification of the Gene Encoding Glycoprotein G, and Evolutionary Comparisons," J. Gen. Virol., 1987, vol. 68, pp. 19-38.

McGeoch et al., The Complete DNA Sequence of the Long Unique Region in the Genome of Herpes Simplex Virus Type I, 1 Gen Virol., 1988, vol. 69, pp. 1531-1574.
Yamada et al., Human Papillornavirtis Type 16 Variant Lineages in United States Populations Characterized by Nucleotide Sequence Analysis of the E6, L2, and LI Coding Segments, J. Virol., Dec. 1995, vol. 69, No. 12, pp. 7743-7753.
Swain et al., Nucleotide Sequence of the Herpes Simplex Virus Type 2 Thymidine Kinase Gene, Virol., Jun. 1983, vol. 46, No. 3, pp. 1045-1050.
Delius et al., Primer-Directed Sequencing of Human Papillomavirus Types, Current Topics in Microbiology and Immunology, 1994, vol. 185, pp. 13-31.
Blair et al., Herpes Simplex Virus Virion Stimulatory Protein mRNA Leader Contains Sequence Elements Which Increase Both Virus-Induced Transcription and mRNA Stability, J Virol., Aug. 1987, vol. 62, No. 2, pp. 444-453.
Larder et al., Related functional domains in virus DNA polymerases, The EMBO J., 1987, vol. 6, No. 1, pp. 169-175.
McGeoch et al., Structures of Herpes Simplex Virus Type 1 Genes Required Replication of Virus DNA, J. Virol., vol. 62, No. 2, pp. 444-453.
Lowe et al.; "A Hybrid-Capture Assay to Detect HPV mRNA Ratios in Cervical Specimens"; Journal of Virological Methods; vol. 179; No. 1; Jan. 2012; pp. 142-147.
International Search Report Based on Application No. PCT/US2012/026380 Mailed Oct. 15, 2012.
International Search Report Based on Application No. PCT/US2012/020684 Mailed Oct. 25, 2012.
Clad et al.; "Performance of the Aptima High-Risk Human Papillomavirus mRNA Assay in a Referral Population in Comparison With Hybrid Capture 2 and Cytoloty"; Journal of Clinical Microbiology; Mar. 2011; LNKD—PubMed:21191046; vol. 49; No. 3; Dec. 29, 2010; pp. 1071-1076; Abstract.
Li et al; Detection of Human Papillomavirus Genotypes With Liquid Bead Microarray in Cervical Lesions of Northern Chinese Patients; Cancer Genetics and Cytogenetics, Elsevier Science Publishing, New York, NY, US; vol. 182; No. 1; Mar. 6, 2008; pp. 12-17; Abstract.
Gheit et al.; "Development of a Sensitive and Specific Assay Combining Multiplex PCR and DNA Microarray Primer Extension to Detect High-Risk Mucosal Human Papillomavirus Types"; Journal of Clinical Microbiology, American Society for Microbiology, Washington, DC, US ; vol. 44; No. 6; Jun. 1, 2006; pp. 2025-2031; Abstract.
Han et al.; "Simultaneous Amplification and Identification of 25 Human Papillomavirus Types With Templex Technology"; Journal of Clinical Microbiology Nov. 2006 US LNKD—DOI:10.1128/JCM. 01762-06; vol. 44; No. 11; Nov. 2006; pp. 4157-4162; Abstract.
Database EMBL [Online]; Jul. 19, 2007; "Sequence 25 From Patent EP1806410"; XP002675256; Retrieved From EBI Accession No. EMBL:CS642417; Database Accession No. CS642417; The Whole Document.
Database EMBL [Online]; Dec. 14, 2010; "Sequence 26 From U.S. Pat. No. 7,812,144"; XP00267527; Retrieved From EBI Accession No. EMBL:GX640151; Database Accession No. GX640151; The Whole Document.
Database Geneseq [Online]; Jan. 22, 2009; "HPV-16 E7/E6 Gene Target Sequence, Bases 752-774"; XP002675258, Retrieved From EBI Accesssion No. GSN:ATS82292; Database Accession No. ATS82292; The Whole Document.
Database Geneseq [Online]; Jan. 22, 2009; "HPV-16 E71E6 Gene Target Sequence, Bases 698-720"; XP002675259 Retrieved From EBI Accession No. GSN:ATS82290; Database Accession No. ATS82290; The Whole Document.
Database Geneseq [Online]; Apr. 1, 2010; "HPV16 E7 Gene Forward RT-PCR Primer SEQ ID 49"; XP002675260; Retrieved From EBI Accession No. GSN:AXU96631; Database Accession No. AXU96631; The Whole Document.
Database Geneseq [Online]; Apr. 21, 2005; "E7 Coding Region (1-87) Amplifying Sense PCR Primer, SEQ ID No. 37"; XP002675261; Retrieved From EBI Accession No. GSN:ADX15568; Database Accession No. ADX15568; Sequence.

(56) References Cited

OTHER PUBLICATIONS

Casademont et al., "Rapid detection of Campylobacter fetus by polymerase chain reaction combined with non-radioactive hybridization using an oligonucleotide covalently bound to microwells." Molecular and Cellular Probes (2000) 14, 233-240.

Chomvarin et al., "Development of EIA for Detection of Chlamydia Trachomatis in Genital Specimens." Department of Microbiology and Department of Pathology, Faculty of Medicine, Khon Kaen University. Mar. 2000, vol. 31, No. 1., 96-103.

Luo et al., "Adiponectin stimulates human osteoblasts proliferation and differentiation via the MAPK signaling pathway," Experimental Cell Research, Academic Press, US, 309:1, (Sep. 10, 2005) 99-109, XP005037411.

Ouitas N. et al., "A Novel ex vivo skin model for the assessment of the potential transcutaneous anti-inflammatory effect of topically applied Harpagophytum procumbens extract," International Journal of Pharmaceutics, Elsevier BV, NL, 376: 1-2, (Jul. 6, 2009), 63-68, XP026185227.

Scholz et al., "Analysis of human immunodeficieny virus matrix domain replacements," Virology, Elsevier, Amsterdam, NL. 371: 2, (Nov. 8, 2007) 322-335, XP022439785.

Xie H. et al., "Apelin in and its receptor are expressed in human obsteoblasts," Regulatory Peptides, Elsevier Science B.V., NL, 134: 2-3, (May 15, 2006), 118-125, XP27895144.

Zhang W. et al., "Bone-Targeted Overespression of Bcl-2 Increases Osteoblast Adhesion and Differentiation and Inhibits of Mineralization In Vitro," Calcified Tissue International, Springer-Verlag, NE, 80: 2, (Feb. 2, 2007), 111-122.

European Office Action dated Jul. 14, 2014, issued in Application No. 10 755 291.1-1406.

European Office Action dated Jul. 4, 2014, issued in Application No. 09 752 940.8-1403.

Japanese Office Action dated Jun. 30, 2014, issued in Application No. 2011-548258.

Chinese Office Action dated May 4, 2014, issued in Application No. 200980143682.9, English translation.

Japanese Notice of Reasons for Rejection dated Aug. 28, 2014, issued in Application No. 2012-508768.

Coutlee et al., "Nonisotopic Detection of RNA in an Enzyme Immunoassay Using a Monoclonal Antibody against DNA-RNA Hybrids." Analytical Biochemistry 181, 153-162 (1989).

Japanese Office Action dated May 27, 2015, issued in Application No. 2013-511335.

Phillips et al., "Simultaneous Detection of C282Y and H63D Hemochromatosis Mutations by Dual-color Probes" Molecular Diagnosis. vol. 6, No. 2: 107-116, (2000).

\* cited by examiner

US 9,422,593 B2

METHODS AND COMPOSITIONS FOR SEQUENCE-SPECIFIC PURIFICATION AND MULTIPLEX ANALYSIS OF NUCLEIC ACIDS

REFERENCE TO RELATED APPLICATIONS

This application claims priority to U.S. Provisional Patent Application No. 61/346,218, filed on May 19, 2010, the entire contents of which are hereby incorporated by reference.

BACKGROUND OF THE INVENTION

1. Field of Invention

The present disclosure relates to methods, compositions, and kits for purifying, detecting, and characterizing nucleic acids.

2. Description of Related Art

The identification of the presence or absence of specific nucleic acid sequences in a sample is a central part of many assays and tests used in the modern research lab and clinical setting. In the typical scheme, the nucleic acids from the sample are first separated from other macromolecules present in the sample by manipulating various physical properties. For example, nucleic acids typically bear a net negative charge at neutral pH, owing to the phosphodiester backbone. This property can be manipulated to separate nucleic acids from other macromolecules using anion exchange resins. As another example, differential solubility of nucleic acids compared to other macromolecules in certain solvents is used to extract nucleic acids from the sample. Numerous other such schemes exist. However, the amount of target nucleic acid relative to the total amount of nucleic acid purified typically is very low. Therefore, some type of amplification is necessary before the target nucleic acid can be detected. Either the amount of specific nucleotide sequence(s) is increased by target amplification methods such as polymerase chain reaction (PCR) or the specific nucleotide sequence(s) is/are reacted with a detectable label and the signal from the label is amplified to detectable levels.

Existing nucleic acid detection assays are usually based on PCR that detects the small portion of genome. The most advanced amplification format is real-time PCR that is performed in 'closed tube format' eliminating the risk of amplicon contamination. Unfortunately, these methods have limited utility. One limitation is that target-specific amplification methods such as PCR are inherently error-prone. For example, although the stringency of primer hybridization can be controlled, there nonetheless exists the potential for non-specific primer binding and primer-independent amplification, which can lead to false-positive results. Moreover, different sequences can amplify at different rates, resulting in amplification bias. As a result, quantitative analysis of multiple nucleic acid sequences in a single reaction often suffers from a lack of sensitivity, resulting in limited multiplex capability. The limitation of this approach is limited multiplex capability of the PCR and potential false negative results if the amplicon region is mutated. Another requirement is that real-time PCR requires complicated thermocycling equipment which could limit its applicability to automated systems. In addition, target nucleic acids that are present at low concentrations relative to other nucleic acids may be effectively "masked" from the polymerase, which could result in false-negative results. Other factors may exist that reduce both the specificity and sensitivity of such assays.

Therefore, methods and compositions are needed for specific and sensitive isolation and analysis of at least one target nucleic acid containing at least one specific sequence.

SUMMARY OF THE INVENTION

The present disclosure in aspects and embodiments addresses these various needs and problems by providing a method of detecting at least one target nucleic acid comprising: (1) sequence-specific isolation of a target nucleic acid from a sample; (2) amplifying the isolated target nucleic acid; and (3) detecting the target nucleic acid using a plurality of detectably labeled nucleic acid detection probes, wherein each (a) bears a different detectable label from the other detection probes, and/or (b) has a different melting temperature from probes bearing the same detectable label. The present disclosure also relates to kits for use in such a method.

In an aspect, the method comprises: A. purifying the at least one target nucleic acid by a method comprising: A1. generating a double-stranded nucleic acid hybrid of the at least one target nucleic acid by hybridizing the at least one target nucleic acid to a hybrid probe set comprising at least a first nucleic acid probe specific for the at least one target nucleic acid; A2. separating the double-stranded nucleic acid hybrid from the sample to generate at least one purified nucleic acid; B. amplifying at least a portion of the at least one purified nucleic acid; and C. detecting the target nucleic acid by a method comprising: C1. contacting the amplified nucleic acid with at least one detection probe set, wherein: C1(a). each of the detection probes of the detection probe set bears a detectable label; C1(b). at least two of the detection probes of the detection probe set carry the same detectable label; and C1(c). each of the probes carrying the same detectable label has a melting temperature ($T_m$) which differs from the other probes with the same label; C2. detecting the amplified nucleic acid by determining whether the labeled probe has hybridized to its nucleic acid sequence; and C3. detecting the temperature at which each detection probe dissociates from the nucleic acid sequence to which it has bound.

In an embodiment, the double-stranded nucleic acid hybrid is separated from the sample by a method comprising contacting the double stranded nucleic acid hybrid with a molecule that binds specifically to double-stranded nucleic acid hybrids, preferably an anti-DNA:RNA hybrid antibody.

In another embodiment, the target is amplified by a method comprising an isothermal amplification, preferably whole genome amplification.

In another embodiment, the amplified nucleic acids are fragmented prior to the contacting them with the detection probe set.

In another embodiment, the target nucleic acid is specific for a pathogen selected from the group consisting of: *Mycobacterium tuberculosis, Streptococcus, Pseudomonas, Shigella, Campylobacter, Salmonella*, Respiratory Syncytial Virus A, Respiratory Syncytial Virus B; adenovirus, HSV1, HSV2, Influenza A/B, hMPV, Parainfluenzavirus 1-4, Coronavirus, Rhinovirus, Enterovirus, Bocavirus, cytomegalovirus (CMV), HIV, H1N1, *chlamydia, Neisseria gonorrhoeae, Trichomonas vaginalis, Staphylococcus aureus*, SARS-associated coronavirus, *Escherichia coli, Bacillus anthracis*, Ebolavirus, Marburgvirus, *Yersinia pestis, Vibrio cholerae, F. tularensis, Brucella, Coxiella burnetii*, Machupo virus, *Coccidioides immitis, Coccidioides posadasii., Burkholderia mallei, Burkholderia pseudomallei, Shigella* ssp. *bacterium, Rickettsia rickettsii, Rickettsia prowazekii, Chlamydophila psittaci*, yellow fever virus, Japanese encephalitis virus, Rift Valley fever virus, Variola major, and Variola minor.

In a further aspect, a kit is disclosed for performing the methods disclosed herein, the kit comprising at least a hybrid probe set and a detection probe set.

DETAILED DESCRIPTION OF THE INVENTION

Figure 1:
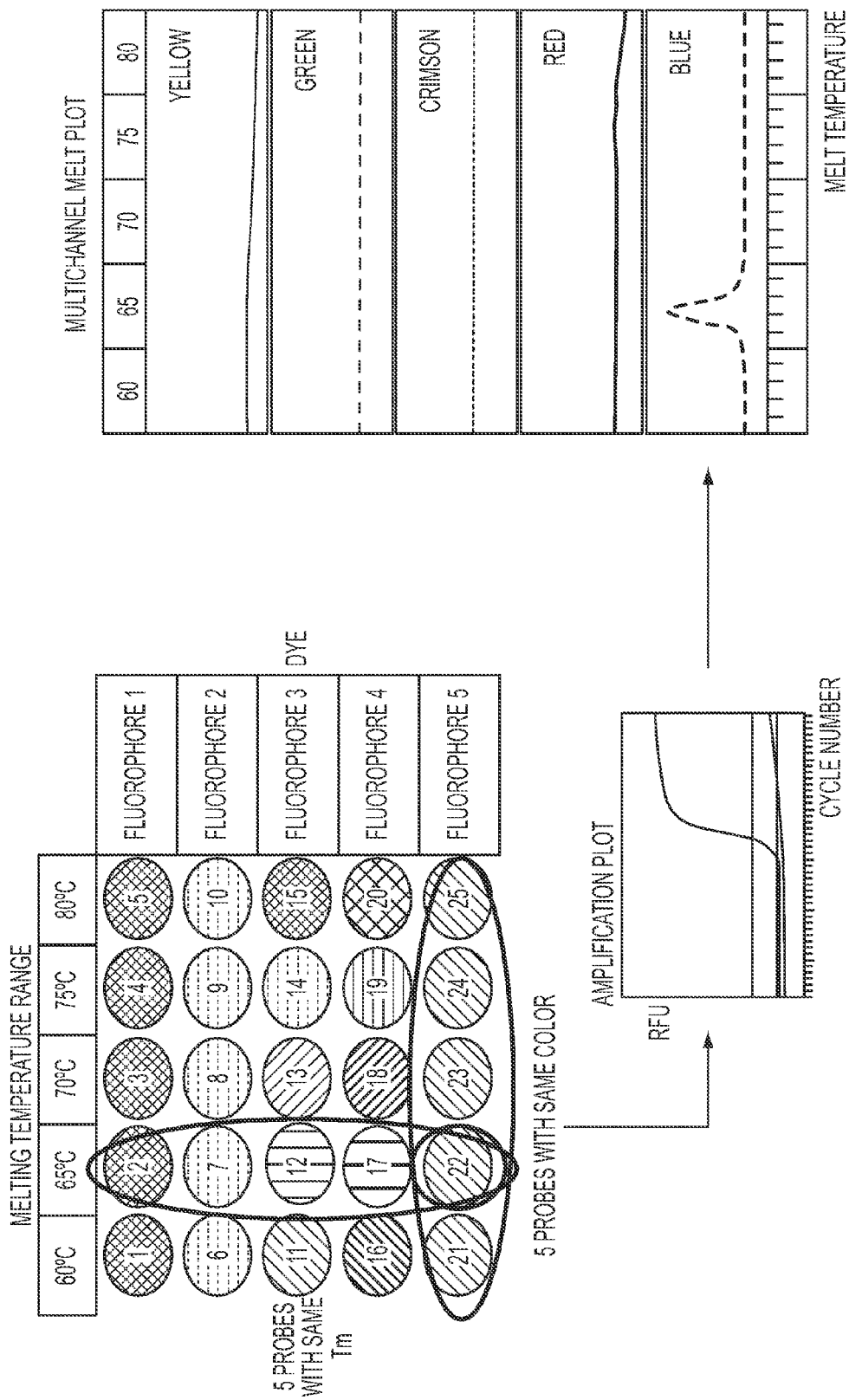
FIG. 1 demonstrates the principle behind TaqMelt™ probes, which may be used with the detection step of the present methods. The reactions performed with the probes in one row all share a common label. However, the melting temperature of the probes differs. It is thus possible to identify each probe by means of the differing melting temperatures. The probes in column 2 for example all have the same melting temperature but a different label. It is thus possible to identify each probe by means of the different label. This format lends itself to single nucleotide polymorphisms ("SNP") detection by creating probes that detect these SNPs by melting at different temperature than the wild type sequence.

The present disclosure covers methods, compositions, reagents, and kits for determining the presence of at least one target nucleic acid in a sample. The methods, compositions, reagents, systems, and kits may be used for clinical diagnostic purposes, including but not limited to the detection and identification of pathogenic organisms and the detection of a genetic predisposition to a particular disease. In other aspects, the methods and compositions may be adapted for use in forensic or biodefense applications.

As used herein the term "probe" is a nucleic acid which is able to bind another nucleic acid.

As used herein the term "tissue" refers to any tissue or fluid in a human, animal or plant including, but not limited to breast, prostate, blood, serum, cerebrospinal fluid, liver, kidney, breast, head and neck, pharynx, thyroid, pancreas, stomach, colon, colorectal, uterus, cervix, bone, bone marrow, testes, brain, neural tissue, ovary, skin, and lung.

As used herein the term "probe set" is a set of three or more agents that may interact with a nucleic acid molecule at a specific position, i.e. sequence.

As used herein, a "label" is a moiety that is bound covalently or non-covalently to a probe where it can give rise to signal which may be detected by optical or other physical means.

In an aspect a method for detecting at least one target nucleic acid in a sample is disclosed, the method comprising: (1) sequence-specific isolation of the target nucleic acid from a sample; (2) amplifying at least a portion of the isolated target nucleic acid; and (3) detecting the target nucleic acid using a plurality of detectably labeled nucleic acid detection probes, wherein each detection probe: (a) bears a different detectable label from the other detection probes, and/or (b) has a different melting temperature from probes bearing the same detectable label.

I. Samples and Sample Preparation

Any sample in which nucleic acids may be present may be used as a starting point, including, without limitation: a specimen or culture (e.g., cellular, microbiological and viral cultures) including clinical and laboratory biological samples; environmental samples, such as water, dust, dirt, and air samples; food and agricultural samples; and forensic samples, including semen, hair, blood, skin, and saliva samples. Biological samples may be from an animal, including a human, fluid, solid (e.g., stool) or tissue, as well as liquid and solid food and feed products and ingredients such as dairy items, vegetables, meat and meat by-products, and waste. Environmental samples include environmental material such as surface matter, soil, water and industrial samples, as well as samples obtained from food and dairy processing instruments, apparatus, equipment, utensils, disposable and non-disposable items.

In another aspect, the sample may comprise, consist, or consist essentially of nucleic acids that have been extracted from a biological sample. Numerous methods are known for extracting nucleic acids from a biological or environmental sample, including but not limited to: phenol/chloroform extraction; anion exchange chromatography; cesium chloride gradient ultracentrifugation; size exclusion chromatography; and silca/chaotropic salt extraction. Extracted nucleic acids may be further separated according to size by gel electrophoresis and extracted from the gel if samples comprising specific nucleic acid sizes are desired.

As noted above, the methods disclosed herein relate to the detection and/or genotyping of at least one target nucleic acid in a sample. The at least one target nucleic acid may be DNA or RNA or both DNA and RNA and can be single-stranded, double-stranded, or partially single-stranded. The at least one target nucleic acid can be contained within a larger nucleic acid. Detection of either the at least one target nucleic acid or the larger nucleic acid comprising the at least one target nucleic acid is contemplated by this disclosure.

In an aspect, the nucleic acid may be naturally occurring or synthetic nucleic acid, including but not limited to: RNA, DNA, cDNA (complementary DNA), LNA (locked nucleic acid), mRNA (messenger RNA), mtRNA (mitochondrial), rRNA (ribosomal RNA), tRNA (transfer RNA), nRNA (nuclear RNA), siRNA (short interfering RNA), snRNA (small nuclear RNA), snoRNA (small nucleolar RNA)1 scaRNA (Small Cajal Body specific RNA), microRNA, dsRNA (doubled-stranded RNA), ribozyme, riboswitch, viral RNA, dsDNA (double-stranded DNA), ssDNA (single-stranded DNA), plasmid DNA, cosmid DNA, chromosomal DNA, viral DNA, mtDNA (mitochondrial DNA), nDNA (nuclear DNA), snDNA (small nuclear DNA) or the like or any other class or sub-class of nucleic acid which is distinguishable from the bulk nucleic acid in a sample.

The at least one target nucleic acids may include, without limitation, nucleic acids found in specimens or cultures (e.g., cellular, microbiological and viral cultures) including biological and environmental samples. The at least one target nucleic acids may be found in biological samples from an animal, including a human, fluid, solid (e.g., stool) or tissue, as well as liquid and solid food and feed products and ingredients such as dairy items, vegetables, meat and meat by-products, and waste. At least one target nucleic acids may be found in environmental samples and include environmental material such as surface matter, soil, water and industrial samples, as well as samples obtained from food and dairy processing instruments, apparatus, equipment, utensils, disposable and non-disposable items.

The at least one target nucleic acids may be from other viral, bacteria, mycobacteria or plasmodia, such as *Mycobacterium tuberculosis, Streptococcus, Pseudomonas, Shigella, Campylobacter, Salmonella*, Respiratory Syncytial Virus A, Respiratory Syncytial Virus B; adenovirus, HSV1, HSV2, Influenza A/B, hMPV Parainfluenzavirus 1-4, Coronavirus, Rhinovirus, Enterovirus, Bocavirus, cytomegalovirus (CMV), HIV, H1N1, *chlamydia, Neisseria gonorrhoeae, Trichomonas vaginalis, Staphylococcus aureus*, SARS-associated coronavirus, *Escherichia coli, Bacillus anthracis*, Ebolavirus, Marburgvirus, *Yersinia pestis, Vibrio cholerae, F. tularensis, Brucella, Coxiella burnetii*, Machupo virus, *Coccidioides immitis, Coccidioides posadasii., Burkholderia mallei, Burkholderia pseudomallei, Shigella* ssp. *bacterium, Rickettsia rickettsii, Rickettsia prowazekii, Chlamydophila psittaci*, yellow fever virus, Japanese encephalitis virus, Rift Valley fever virus, Variola major, and Variola minor.

In an aspect the at least one target nucleic acids are at least 70%, at least 80%, at least 85%, at least 90%, at least 95%, at least 96%, at least 97%, at least 98%, at least 98%, at least 99%, or 100% identical to nucleic acids associated with any one of cervical samples (e.g., a sample obtained from a cervical swab) or cervical cell samples, adenoid cells, anal epithelial cells, blood, saliva, cerebral spinal fluid, pleural fluid, milk, lymph, sputum, urine and semen, other viral, bacteria, mycobacteria or plasmodia, for example *Mycobacterium tuberculosis, Streptococcus, Pseudomonas, Shigella, Campylobacter, Salmonella*, Respiratory Syncytial Virus A, Respiratory Syncytial Virus B; adenovirus, HSV1, HSV2, Influenza A/B, hMPV Parainfluenzavirus 1-4, Coronavirus, Rhinovirus, Enterovirus, Bocavirus, cytomegalovirus (CMV), HIV, H1N1, *chlamydia, Neisseria gonorrhoeae, Trichomonas vaginalis, Staphylococcus aureus*, SARS-associated coronavirus, *Escherichia coli, Bacillus anthracis*, Ebolavirus, Marburgvirus, *Yersinia pestis, Vibrio cholerae, F. tularensis, Brucella, Coxiella burnetii*, Machupo virus, *Coccidioides immitis, Coccidioides posadasii., Burkholderia mallei, Burkholderia pseudomallei, Shigella* ssp. *bacterium, Rickettsia rickettsii, Rickettsia prowazekii, Chlamydophila psittaci*, yellow fever virus, Japanese encephalitis virus, Rift Valley fever virus, Variola major, and Variola minor.

In one aspect, the at least one target nucleic acid is an HPV nucleic acid. In another aspect, the HPV nucleic acid is HPV DNA of a HR-HPV type. In another aspect, the HPV nucleic acid is HPV RNA of a LR-HPV type. In another aspect the at least one target nucleic acids are any one of HR-HPV types 16, 18, 26, 31, 33, 35, 39, 45, 51, 52, 56, 58, 59, 66, 68, and 82 or any one of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91.

In another aspect, a plurality of target nucleic acid is targeted. In one aspect, the plurality of target nucleic acids consists of a set of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleic acids having distinct nucleotide sequences. Any set of nucleic acids to be targeted can be used. In one aspect, the plurality of target nucleic acids is selected such that each is related to the others. By way of example and not limitation, the set of nucleic acids can be: structurally related to one another (for example, members of a gene family); functionally related to one another (for example, nucleic acids encoding proinflammatory cytokines); phylogenetically related to one another (for example, nucleic acids specific for different members of a family of viruses, such as HPV-family viruses); related by virtue of differential expression in a different cell or tissue type (for example, macrophage-associated nucleic acids and prostate-associated nucleic acids) or disease states (cervical cancer associated nucleic acids). In another aspect, the set of nucleic acids is unrelated.

In one aspect, a set of target nucleic acids comprises, consists, or consists essentially of HR-HPV types 16, 18, 26, 31, 33, 35, 39, 45, 51, 52, 56, 58, 59, 66, 68, and 82, or any subset thereof. In another aspect, a set of target nucleic acids comprises, consists, or consists essentially of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91, or any subset thereof. In another aspect a set of target nucleic acids comprises, consists, or consists essentially of HR-HPV types 16, 18, 26, 31, 33, 35, 39, 45, 51, 52, 56, 58, 59, 66, 68, and 82, or any subset thereof; and LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91, or any subset thereof. In another aspect, the at least one target nucleic acid is at least 70%, at least 80%, at least 85%, at least 90%, at least 95%, at least 96%, at least 97%, at least 98%, at least 98%, at least 99%, or 100% identical to nucleic acids associated with any one of HPV, genetic variants of HPV, HPV DNA of a HR-HPV type, or HPV RNA of a HR-HPV type. In another aspect the at least one target nucleic acids are at least 70%, at least 80%, at least 85%, at least 90%, at least 95%, at least 96%, at least 97%, at least 98%, at least 98%, at least 99%, or 100% identical to nucleic acids associated with any one of HR-HPV types 16, 18, 26, 31, 33, 35, 39, 45, 51, 52, 56, 58, 59, 66, 68, and 82 or any one of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91.

In another aspect, a target nucleic acid is chosen that is: not more than from 35% to 65% GC AT rich; from 40% to 60% GC rich; from 45% to 55% GC rich; or from 50% to 65% GC rich. In another aspect, a target nucleic acid is selected that does not near neighbor, cross-reactive variants or species.

After the sample is collected, the sample may be treated with a denaturation reagent to render the at least one target nucleic acid accessible to hybridization. In one aspect, the sample is denatured with an alkaline solution. Without being limited, suitable alkali include NaOH and KOH.

Alkaline treatment of protein effectively homogenizes the specimen to ensure reproducibility of analysis results for a given sample. It can also reduce the viscosity of the sample to increase kinetics, homogenize the sample, and reduce background by destroying any endogenous single stranded RNA nucleic acids, DNA-RNA hybrids or RNA-RNA hybrids in the sample. It also helps inactivate enzymes such as RNases and DNases that may be present in the sample. One skilled in that art would appreciate that if RNA is the at least one target nucleic acid (as opposed to DNA), different reagents may be preferable including, but not limited to phenol extraction and TCA/acetone precipitation, and guanidinium thiocyanate-phenol-chloroform extraction.

Other methods of denaturation may be employed such as utilizing a heating step, for example, heating the sample to about 95° C. to separate the strands of nucleic acid. Enzymes such as helicase may be used as well.

II. Purifying Step

In an aspect, the sequence-specific purification step comprises: (1) generating a double-stranded nucleic acid hybrid of the target nucleic acid by hybridizing at least one nucleic acid probe to the target nucleic acid to specific for the at least one target nucleic acid and (2) separating the double-stranded nucleic acid hybrid from the sample to generate a purified target nucleic acid.

After the sample comprising the nucleic acid is prepared for hybridization, it is contacted with at least one polynucleotide hybrid capture probe under a condition sufficient for the hybrid capture probes to hybridize to its complement. The at least one polynucleotide hybrid probe can be full length, truncated, or synthetic DNA or full length, truncated, or synthetic RNA. If the at least one target nucleic acid is DNA, then the at least one polynucleotide hybrid probe may be RNA and if the at least one target nucleic acid is RNA, then the probe may be DNA.

In one aspect, a single polynucleotide probe is used in the purification step. The single polynucleotide hybrid capture probe may be specific for only a single target nucleic acid or may be designed so as to hybridize to a plurality of target nucleic acids under stringent conditions. By way of example and not limitation, a polynucleotide probe may be designed against a highly conserved region of a genus of related nucleic acids, such that the polynucleotide probe would be expected to hybridize under stringent conditions to substantially all nucleic acids of that genus.

In another aspect, a plurality of polynucleotide probes is used in the purification step. The plurality of polynucleotide probes may be specific for only a single target nucleic acid or may be specific for a plurality of target nucleic acids. By way of example and not limitation, a plurality of polynucleotide probes specific for a single target nucleic acid may be generated by fragmenting the target nucleic acid. In one aspect, at least one polynucleotide hybrid probe is provided for each target nucleic acid. In another aspect, at least two polynucleotide hybrid probes are provided for each target nucleic acid.

In an aspect, the polynucleotide hybrid probe is capable of hybridizing or binding to nucleic acids at least 70%, at least 80%, at least 85%, at least 90%, at least 95%, at least 96%, at least 97%, at least 98%, at least 98%, at least 99%, or 100% identical to nucleic acids associated with HPV, genetic variants of HPV, HPV DNA of a HR-HPV type, or HPV RNA of a HR-HPV type, or any one of one of HR-HPV types 16, 18, 26, 31, 33, 35, 39, 45, 51, 52, 56, 58, 59, 66, 68, and 82 or any one of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91. In another aspect, the probe is complementary to HPV, genetic variants of HPV, HPV DNA of a HR-HPV type, HPV RNA of a HR-HPV type, or any one of one of HR-HPV types 16, 18, 26, 31, 33, 35, 39, 45, 51, 52, 56, 58, 59, 66, 68, and 82 or any one of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91.

In another aspect, a plurality of polynucleotide hybrid probes is provided, the plurality being selected to hybridize to and purify each of a set of target nucleic acids. In one aspect, the plurality of polynucleotide hybrid probes is capable of hybridizing to each nucleic acid of a set of target nucleic acids consisting of HR-HPV types 16, 18, 26, 31, 33, 35, 39, 45, 51, 52, 56, 58, 59, 66, 68, and 82 nucleic acids, or any subset thereof. In one aspect, the plurality of polynucleotide hybrid probes is capable of hybridizing to each nucleic acid of a set of target nucleic acids consisting of LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91, or any subset thereof. In one aspect, the plurality of polynucleotide hybrid probes is capable of hybridizing to each nucleic acid of a set of target nucleic acids consisting of HR-HPV types 16, 18, 26, 31, 33, 35, 39, 45, 51, 52, 56, 58, 59, 66, 68, and 82, or any subset thereof; and LR-HPV types 2, 3, 6, 7, 10, 11, 13, 27, 28, 30, 32, 40, 42, 43, 53, 54, 55, 61, 62, 67, 69, 70, 71, 72, 74, 81, 83, 84, 85, 86, 87, 89, 90, and 91, or any subset thereof.

If the at least one target nucleic acid was denatured using an alkaline treatment, the one or more polynucleotide probes may be diluted in a probe diluent that also can act as a neutralizing hybridization buffer (to neutralize the basic denaturation reagent).

The probe diluent used for DNA or RNA probes may differ due to the different requirements necessary for DNA versus RNA stability. For example, if the probes are RNA, it is preferable to neutralize the sample first and then add the probe or alternatively, add the RNA probe and neutralizing agent (probe diluent) to the sample at the same time as excessive alkalinity can destroy RNA. The probe diluent can be used to dissolve and dilute the probe and also help restore the sample to about a neutral pH, e.g., about pH 6 to about pH 9, to provide a more favorable environment for hybridization. Sufficient volume of probe diluent, preferably one-half volume of the sample, may be used to neutralize the base-treated sample.

For full length probes, a heated alkaline solution may be added to the sample, then probe diluent may be added to the sample at room temperature, and then the sample may be reheated. Such a process can inhibit secondary structure from forming. Antibodies tend to irreversibly bind to structures with secondary structure. When using non-full length probes such as truncated or synthetic probes, heating the solutions or sample may not be necessary because secondary structures issues are not present. In an aspect, the sample is not heated when used with truncated or synthetic probes.

After treatment with the denaturation reagent, an aliquot of neutralization buffer, in an aspect the probe diluent described, in which the one or more probes are dissolved, can be added to the sample under appropriate conditions to allow hybridization or binding of the probe and the at least one target nucleic acid to occur. The neutralization buffer may contain a single buffering salt. In an aspect, the neutralization buffer does not contain more than a single buffering salt. The hybridization condition is sufficient to allow the one or more polynucleotide probes to anneal to a corresponding complementary nucleic acid sequence, if present, in the sample to form a double-stranded nucleic acid hybrid.

Hybridization conditions suitable for the particular probes and diluents described herein are employed. For example, the probes and sample nucleic acids can be incubated for a hybridization time, preferably at least about 5 to about 30 minutes, about 5 to about 20 minutes, or from about 7 to about 15 minutes, or about 10 minutes, as well as any number within the recited ranges sufficient to allow the one or more polynucleotide probes to anneal to a corresponding complementary nucleic acid sequence. The hybridization condition can include a hybridization temperature of at least about 65° C., about 68.5° C., and about 67° C. to about 70° C., as well as any number within the recited ranges. For a given at least one target nucleic acid and a given probe, one of ordinary skill in the art can readily determine desired hybridization conditions by routine experimentation. One of ordinary skill in the art will further appreciate that the time and temperature of hybridization must be optimized, one with respect to the other. Thus, higher hybridization temperatures may be carried out for shorter periods of time and vice versa. Without being limited, stringent hybridization conditions may be controlled by increasing the temperature, increasing the ionic conditions to above 0.5M (for example, NaCl), or reducing the concentration of PAA. As a non-limiting example, stringent hybridization conditions may include performing a hybridization reaction at elevated temperatures, such as of at least about 65° C., at least about 68.5° C., between about 67° C. to about 70° C. , and between about 69° C. to about 70° C. Stringent hybridization conditions may also include elevated temperatures, such as of at least about 65° C., at least about 68.5° C., and between about 67° C. to about 70° C.

In one aspect, the sample is suspended in collection medium, the at least one target nucleic acid is denatured with a denaturation reagent, and hybridized to nucleic acid probes suspended in a neutralizing buffer. In another aspect the neutralizing buffer is the probe diluent. In another aspect, the probe diluent comprises 2.2 M BES (N,N-bis(2-hydroxyethyl)-2-aminoethanesulfonic acid), 2.6% polyacrylic acid, 0.7 N NaOH and 0.05% sodium azide.

In an aspect, sequence-specific purification of the target nucleic acid is performed using hybrid capture. Hybrid capture refers to a method of isolating and analyzing nucleic acids the generation of DNA:RNA hybrids and isolation of the DNA:RNA hybrid through the use of a molecule that binds specifically to DNA:RNA hybrids. Various aspects of hybrid capture are described in: Nazarenko et al., A novel method of HPV genotyping using Hybrid Capture® sample preparation method combined with GP5+/6+ PCR and multiplex detection on Luminex® XMAP®, Journal of Virological Methods 154 (2008) 76-81; and Nazarenko et al., U.S. Pat. No. 7,601,497, each of which is hereby incorporated by reference in its entirety.

Molecules specific for the double-stranded nucleic acid hybrids include, but are not limited to, monoclonal antibodies, polyclonal antibodies, proteins such as but not limited to RNAse H, nucleic acids including but not limited to aptamers, or sequence specific nucleic acids. Aptamers are short stretches of random sequences that are successively selected from a library of sequences by hybridizing to a target, amplifying the hybridized aptamers, and repeating the selection process.

In one aspect the molecule specific for the double-stranded nucleic acid hybrid is captured by an antibody, known as an anti-hybrid antibody. In another aspect, the anti-hybrid antibodies are immobilized onto a support before the double-stranded nucleic acid hybrid is captured. Methods of immobilizing antibodies to solid supports are well known in the art. By way of examples and not limitation, the antibodies can be covalently linked to the solid support. As another example, the antibody can be adsorbed onto the support by, for example, protein-protein interactions, protein-G beads, biotin-streptavidin interaction, EDAC to link to a carboxyl or tosyl group, etc., or hybridization directly onto the solid support using, for example, sequence specific nucleic acids in an affinity column.

In another aspect, the anti-hybrid antibodies may be complexed with the double-stranded nucleic acid hybrid before being immobilized on the solid support. By way of example and not limitation the anti-hybrid antibody may be conjugated with a biotin label, while the support may be conjugated with a streptavidin moiety. Anti-hybrid antibody/double-stranded nucleic acid-hybrid complexes can then be allowed in the absence of the solid support. When the solid support is added to the reaction mixture, the anti-hybrid antibody/double-stranded nucleic acid-hybrid complexes will be immobilized to the solid support by virtue of the interaction between the biotin conjugate and the streptavidin moiety.

Supports include but are not limited to beads; magnetic beads, including paramagnetic, diamagnetic, ferromagnetic beads, columns, plates, filter paper, polydimethylsiloxane (PDMS); dipsticks; coated tubes, plates, and dishes; and resin columns. Any support can be used as long as it allows extraction of the liquid phase and provides the ability to separate out bound and unbound antibodies. Paramagnetic beads are particularly useful in that they can be left in the solution and the liquid phase can be extracted or decanted, if a magnetic field is applied to immobilize the beads. Other beads that employ charge switching or silica capture (as opposed to magnetic fields) may be used as well.

The hybrids are incubated with the anti-hybrid antibody attached to the support for a sufficient amount of time to allow capture of the double-stranded nucleic acid hybrids by the immobilized anti-hybrid antibodies. In an aspect, the support is a bead.

The anti-hybrid antibody may be monoclonal or polyclonal. In one aspect the antibody is monoclonal. In one aspect, the antibody is coupled to support by a 1-ethyl-3-[3-dimethylaminopropyl]carbodiimide hydrochloride (EDAC) linker. In one aspect, the support is a polystyrene bead. In an aspect, the support or bead coupled to the antibody is diluted in a bead dilution buffer. The bead dilution buffer is helpful in minimizing protein denaturation on the bead. One example of a bead dilution buffer comprises 6% casein, 100 mM Tris-HCl, 300 mM NaCl, and 0.05% sodium azide.

In an aspect, the beads coated with the anti-hybrid antibody are incubated with the sample at about 67° C. to about 70° C. for about 30 minutes. In another aspect, the beads and sample are incubated at about 68° C. to about 69° C. for about 30 minutes. In yet another aspect, the beads and sample are incubated at about 68.5° C. for 30 minutes. The incubation time can range from about 5 minutes to about 60 minutes, from about 15 minutes to about 45 minutes, from about 20 minutes to about 40 minutes, or any number within the recited ranges, and is generally inversely proportional to the temperature. It will be understood by those skilled in the art that the incubation time, temperature and/or shaking conditions can be varied to achieve alternative capture kinetics as desired.

Following capture of the at least one target nucleic acid/probe hybrid as described above, the captured hybrid may be separated from the rest of the sample by washing away of non-captured nucleic acids.

III. Amplification Step

Once the at least one target nucleic acid is purified, it is amplified. Amplification is performed at this time to increase the sensitivity of the method by increasing the amount of the at least one target nucleic acid.

Various amplification methods may be applied, these are for example, rolling circle amplification (such as in Liu, et al., "Rolling circle DNA synthesis: Small circular oligonucleotides as efficient templates for DNA polymerases," J. Am, Chem. Soc. 118:1587-1594 (1996).), isothermal amplification (such as in Walker, et al., "Strand displacement amplification-an isothermal, in vitro DNA amplification technique", Nucleic Acids Res. 20(7): 1691 -6 (1992)), Ligase chain reaction (such as in Landegren, et al., 11A Ligase-Mediated Gene Detection Technique," Science 241 :1077-1080, 1988, or, in Wiedmann, et ai., "Ligase Chain Reaction (LCR)— Overview and Applications," PCR Methods and Applications (Cold Spring Harbor Laboratory Press, Cold Spring Harbor Laboratory, NY1 1994) pp. S51-S64.).

Nucleic acid amplifications can be broadly separated into two categories: temperature cycled amplifications and isothermic amplifications.

In temperature cycled amplifications, the temperature typically is raised above the melting point of the target nucleic acid to "melt" any double stranded portions, and then lowered to a point at which oligonucleotide primers anneal with a single stranded portion of the target nucleic acid, then raised again to a temperature at which the primers remain annealed and the polymerase is active.

In isothermic amplifications, an agent is added to the reaction mixture to permit amplification without temperature cycling. For example, in helicase-dependant amplification ("HDA"), an enzyme having helicase activity is added to the amplification mixture. As used herein, "helicase" or "an enzyme with, or having, helicase activity" refers to any enzyme capable of unwinding a double stranded nucleic acid. The helicase functions to unwind double stranded nucleic acids, thus obviating the need for repeated melting cycles. Examplary helicases include *E. coli* helicase I, II, III, & IV, Rep, DnaB, PriA, PcrA, T4 Gp41 helicase, T4 Dda helicase, T7 Gp4 helicases, SV40 Large T antigen, yeast RAD. Additional helicases that may be useful include RecQ helicase, thermostable UvrD helicases from *T. tengcongensis* and *T. thermophilus*, thermostable DnaB helicase from *T. aquaticus*, and MCM helicase from archaeal and eukaryotic organisms. As another example, in nick-initiated amplification ("NIA"), a nick-inducing agent is used to induce breaks in the phosphodiester bonds of the nucleic acid backbone. A polymerase having strand displacement activity can then initiate amplification at the site of the nick, using one strand of the nucleic acid as a primer and the other strand as a template. As used herein, "nick-inducing agent" refers to any enzymatic or chemical reagent or physical treatment that introduces breaks in the phosphodiester bond between two adjacent nucleotides in one strand of a double-stranded nucleic acid. Examples of nick-inducing enzymes include Bpu10 I, BstNB I, Alw I, BbvC I, BbvC I, Bsm I, BsrD, and *E. coli* endonuclease I.

The amplification in the disclosed methods can be either a temperature cycled amplification or an isothermic amplification. Exemplary methods of amplification include, but are not limited to: polymerase chain reaction ("PCR"), reverse transcriptase ("RT") reaction, RT-PCR, HDA, RT-HDA, thermophilic helicase-dependent amplification ("tHDA"), RT-tHDA, whole genome amplification ("WGA"), RT-WGA, ligase chain reaction ("LCR"), RT-LCR, NIA, and RT-NIA.

Amplification reactions can further be separated into sequence-dependent or sequence-independent amplifications.

"Sequence-dependent amplification" refers to specific amplification of a target sequence relative to non-target sequences present in a sample with the use of target-specific primers. As used herein, "target-specific primer" refers to a single stranded nucleic acid capable of binding to a pre-determined single stranded region on a target nucleic acid to facilitate polymerase dependent replication of the target nucleic acid to be selectively amplified.

In one aspect, the amplification is a sequence-specific amplification. In another aspect, a pair of target-specific primers, one hybridizing to the 5'-flank of a target sequence within each target nucleic acid and the other hybridizing to the 3'-flank of the target sequence, are used to achieve exponential amplification of the target sequence. Thus arrangement is useful where all of the target nucleic acids comprise a variable region that is sought to be genotyped and where the variable region is flanked on both sides by conserved regions. In another aspect, multiple pairs of target-specific primers are utilized in a single reaction for amplifying multiple targets nucleic acids simultaneously.

Generally, suitable target-specific primer pairs are short synthetic oligonucleotides, for example having a length of more than 10 nucleotides and less than 50 nucleotides. Target-specific, oligonucleotide primer design involves various parameters such as string-based alignment scores, melting temperature, primer length and GC content. When designing a target-specific primer, one of the important factors is to choose a sequence within the target fragment that is specific to the nucleic acid molecule to be amplified. Another important factor is to calculate the melting temperature of a target-specific primer for the reaction. The melting temperature of a target-specific primer is determined by the length and GC content of that oligonucleotide. In one aspect, the melting temperature of the primer is about 10° to 30° C. higher than the temperature at which primer hybridization and target amplification will take place.

"Primer hybridization" refers to binding of an oligonucleotide primer to a region of the single-stranded nucleic acid template under the conditions in which the primer binds only specifically to its complementary sequence on one of the template strands, not other regions in the template. The specificity of hybridization may be influenced by the length of the oligonucleotide primer, the temperature in which the hybridization reaction is performed, the ionic strength, and the pH of the reaction mixture.

Each target-specific primer hybridizes to each end of the target nucleic acid and may be extended in a 3'→5' direction by a polymerase using the target nucleotide sequence as a template. To achieve specific amplification, a homologous or perfect match target-specific primer is preferred. However, target-specific primers may include sequences at the 5' end which are non-complementary to the target nucleotide sequence(s). Alternatively, target-specific primers may contain nucleotides or sequences throughout that are not exactly complementary to the target nucleic acid.

The target-specific primers may include any of the deoxyribonucleotide bases A, T, G or C and/or one or more ribonucleotide bases, A, C, U, G and/or one or more modified nucleotide (deoxyribonucleotide or ribonucleotide) wherein the modification does not prevent hybridization of the primer to the nucleic acid or elongation of the target-specific primer or denaturation of double stranded molecules. Target-specific primers may be modified with chemical groups such as phosphorothioates or methylphosphonates or with non nucleotide linkers to enhance their performance or to facilitate the characterization of amplification products.

In general, the temperature of denaturation suitable for permitting specificity of target-specific primer-template recognition and subsequent annealing may occur over a range of temperatures, for example 20° C. to 75° C. A preferred denaturation temperature may be selected according to which helicase is selected for the melting process. Tests to determine optimum temperatures for amplification of a nucleic acid in the presence of a selected helicase can be determined by routine experimentation by varying the temperature of the reaction mixture and comparing amplification products using gel electrophoresis.

In a further aspect, amplification is a sequence-independent amplification. As used herein, "sequence-independent amplification" refers to any amplification that does not amplify a specific sequence. By way of example and not limitation, random primer mixtures or nick-inducing agents may be used to initiate sequence-independent amplification.

As used herein, "random primer mixture" refers to mixtures of short randomly generated oligonucleotide sequences.

As used herein, "nick-initiated polymerase activity" refers to polymerase activity in the absence of exogenous primers, which is initiated by single-strand breaks in the template. Synthesis initiates at the single-strand break in the DNA, rather than at the terminus of an exogenous synthetic primer. With nick-initiated synthesis, removal of primers is unnecessary, reducing cost, handling time and potential for loss or degradation of the product. In addition, nick-initiated synthesis reduces false amplification signals caused by self-extension of primers. The nicks may be introduced at defined locations, by using enzymes that nick at a recognition sequence, or may be introduced randomly in a target polynucleotide. As used herein, "nick-inducing agent" refers to any enzymatic or chemical reagent or physical treatment that introduce breaks in the phosphodiester bond between two adjacent nucleotides in one strand of a double-stranded nucleic acid. Examples of nick-inducing enzymes include Bpu10 I, BstNB I, Alw I, BbvC I, BbvC I, Bsm I, BsrD, and *E. coli* endonuclease I. In one aspect, at least one nick-inducing enzyme is included as a replacement for a helicase in a reaction mixture. In another aspect, at least one nick-inducing enzyme is added to a reaction mixture in addition to at least one helicase.

In one aspect, the amplification is an isothermic amplification. In another aspect, the isothermic amplification is a Whole Genome Amplification ("WGA"). WGA is an isothermal process that uses non-specific primers to generate amplicons using the target nucleic acid sequence as a template. As multiple random primers are used, substantially the entire molecule comprising the target nucleic acid can be amplified using WGA. For example, Phi 29 DNA polymerase can be used in combination with non-specific primers to amplify target nucleic acid sequences. The polymerase can move along the target nucleic acid sequence displacing the complementary strand. The displaced strand becomes a template for replication allowing high yields of high-molecular weight DNA to be generated. In one aspect, the WGA reaction is modified to include at least one helicase, at least one nick-inducing agent, or both. Various aspects of WGA are described in, Nazarenko et al., U.S. Pat. No. 7,601,497, which is hereby incorporated by reference in its entirety.

IV. Detection Step

The target nucleic acid is detected from the pool of amplified nucleic acids by (1) contacting it with at least one detection probe set comprising a plurality of polynucleotide detection probes under a condition sufficient for each of the detection probes to hybridize to its complement; (2) detecting hybridization of at least one of the polynucleotide detection probes; and (3) determining the melting temperature of ($T_m$) of the polynucleotide detection probe hybridized to the target nucleic acid. The polynucleotide detection probes of the detection probe set can be full length, truncated, or synthetic DNA or full length, truncated, or synthetic RNA. The at least one capture probe may be DNA, RNA, synRNA, or PNA, regardless of the identity of the at least one target nucleic acid. The polynucleotide detection probes should be detectably labeled or adapted so that they may accept a detectable label. Additionally, the detection probe set should be constituted so that: (1) at least two of the plurality of detection probes bear the same detectable label; (2) at least two of the plurality of detection probes bear different detectable labels; and (3) any of the plurality of detection probes bearing the same detectable label have different melting temperatures ($T_m$).

Hybridization conditions suitable for the particular probes and diluents described herein are employed. For example, the probes and sample nucleic acids can be incubated for a hybridization time, preferably at least about 5 to about 30 minutes, about 5 to about 20 minutes, or from about 7 to about 15 minutes, or about 10 minutes, as well as any number within the recited ranges sufficient to allow the one or more polynucleotide probes to anneal to a corresponding complementary nucleic acid sequence. The hybridization condition can include a hybridization temperature of at least about 65° C., about 68.5° C., and about 67° C. to about 70° C., as well as any number within the recited ranges. For a given at least one target nucleic acid and a given probe, one of ordinary skill in the art can readily determine desired hybridization conditions by routine experimentation. One of ordinary skill in the art will further appreciate that the time and temperature of hybridization must be optimized, one with respect to the other. Thus, higher hybridization temperatures may be carried out for shorter periods of time and vice versa. Without being limited, stringent hybridization conditions may be controlled by increasing the temperature, increasing the ionic conditions to above 0.5M (for example, NaCl), or reducing the concentration of PAA. As a non-limiting example, stringent hybridization conditions may include performing a hybridization reaction at elevated temperatures, such as of at least about 65° C., at least about 68.5° C., between about 67° C. to about 70° C., and between about 69° C. to about 70° C. Stringent hybridization conditions may also include elevated temperatures, such as of at least about 65° C., at least about 68.5° C., and between about 67° C. to about 70° C.

All probes used herein (including hybrid capture and detection probes) may be short synthetic RNA probes that specifically bind only to the at least one target nucleic acid. Examples are described in U.S. patent application Ser. No. 12/426,076, filed on Apr. 17, 2009, the contents of which are incorporated herein by reference in its entirety.

In an aspect, the detection step comprises: (1) contacting the amplified nucleic acids with a detection probe set comprising at least four detection probes, wherein (a) each of the detection probes is specific for a nucleic acid sequence; (b) at least two of the detection probes carry the same label; and (c) each of the probes that carry the same label has a melting temperature ($T_m$) which differs by at least 2° C. from the other probes with the same label when they are dissociated from their target nucleic acid sequence by heating; (2) detecting the target nucleic acid by determining whether a labeled probe has bound its nucleic acid sequence; and (3) detecting the temperature at which each given labeled probe dissociates from the nucleic acid sequence to which it has bound. A similar method was previously described in WO2009135832, which hereby is incorporated by reference in its entirety.

In an embodiment, the detection probe set comprises at least four detection probes, wherein at least two detection probes carry the same label.

In another embodiment, the detection probe set comprises at least four detection probes, wherein at least three detection probes carry the same label.

In another embodiment, the detection probe set comprises at least five detection probes, wherein at least two detection probes carry the same label.

In another embodiment, the detection probe set comprises at least five detection probes, wherein at least three detection probes carry the same label.

In another embodiment, the detection probe set comprises at least five detection probes, wherein at least four detection probes carry the same label.

In another embodiment, the detection probe set comprises at least six detection probes, wherein at least two detection probes carry the same label.

In another embodiment, the detection probe set comprises at least six detection probes, wherein at least three detection probes carry the same label.

In another embodiment, the detection probe set comprises at least six detection probes, wherein at least four detection probes carry the same label.

In another embodiment, the detection probe set comprises at least seven detection probes, wherein at least two detection probes carry the same label.

In another embodiment, the detection probe set comprises at least seven detection probes, wherein at least three detection probes carry the same label.

In another embodiment, the detection probe set comprises at least seven detection probes, wherein at least four detection probes carry the same label.

In another embodiment, the detection probe set comprises at least eight detection probes, wherein at least two detection probes carry the same label.

In another embodiment, the detection probe set comprises at least eight detection probes, wherein at least three detection probes carry the same label.

In another embodiment, the detection probe set comprises at least eight detection probes, wherein at least four detection probes carry the same label.

The labels of the detection probes may be fluorescent labels. Where fluorescent labels are used, two or more labels shall be deemed "the same label" when they have maximum emission wavelengths that differ by 0° C. to about 10° C.

In one embodiment, detection probes with the same label have melting temperatures that differ by at least about 2° C., at least about 5° C., from about 5° to about 10° C., from about 5° C. to about 8° C., from about 5° C. to about 7° C., from about 5° to about 6° C. Herein, in the context of temperature values, the term "about" is to be understood as to include deviations of up to +/−10% of the temperature value.

In one embodiment, the detection step comprises: (1) contacting the amplified nucleic acids with at least two detection probe sets, wherein (a) each detection probe set consists of at least three detection probes, (b) each of the detection probes is specific for a nucleic acid sequence, (c) each of the detection probes in a given detection probe set carries a different label, and (d) all of the detection probes in a given detection probe set have a similar or identical melting temperature ($T_m$) when they are dissociated from their target nucleic acid sequence by heating; (2) detecting the amplified nucleic acids by determining whether the labeled detection probe has bound its nucleic acid sequence; and (3) detecting the temperature at which each given labeled detection probe dissociates from the nucleic acid sequence to which it has bound.

In a further embodiment the method comprises at least three detection probe sets, wherein each detection probe set consists of at least three detection probes.

A detection probe set comprises at least 3 detection probes. A detection probe set may be seen as all those detection probes that share a common label but also as all those detection probes that share a common melting temperature (Tm). Ideally, the detection probes in a detection probe set that have the same label or labels that are not distinguishable from one another have different melting temperatures. The detection probes in a detection probe set that have identical or very similar melting temperatures should have different labels.

Using the methods disclosed herein, multiplex detection of 20 different target nucleic acids may be performed in a single reaction. In one embodiment 5 different labels are used and all the detection probes that share a common label have a slightly varying melting temperature. All the detection probes that share a common melting temperature on the other hand have a different label. By detecting the label and the melting temperature either during or after amplification the inventors have for the first time provided for a means which makes it possible to analyze, e.g. said 20 templates in one tube.

In principle this "detecting the amplified nucleic acids by determining whether the labeled probe has bound its nucleic acid sequence", and "detecting the temperature at which each given labeled probe dissociates from the nucleic acid sequence to which it has bound" may be done at the end of given reaction or during the reaction.

The labels of the detection probes in the first and second or further detection probe sets are fluorescent labels and have an emission wavelength that is very similar. Ideally, that means they may be detected without altering the wavelength adjustment that may be detected by the detection device. It is preferred that the labels of the probes in the first, second and third or further detection probe set are identical.

In one embodiment, the labels are fluorescent labels selected from the group of FAM (5-or 6-carboxyfluorescein), VIC, NED, Fluorescein, FITC1 1RD-700/800, CY3, CY5, CY3.5, CY5.5, HEX, TET, TAMRA1 JOE, ROX, BODIPY TMR, Oregon Green, Rhodamine Green, Rhodamine Red, Texas Red, Yakima Yellow, Alexa Fluor PET, Biosearch Blue™, Marina Blue®, Bothell Blue®, Alexa Fluor® 350 FAM™, SYBR® Green 1, Fluorescein, EvaGreen™, Alexa Fluor® 488 JOE™, VIC™, HEX™, TET™, CAL Fluor® Gold 540, Yakima Yellow®, ROX™, CAL Fluor®' Red 610, Cy3.5™, Texas Red®, Alexa Fluor® 568 Cy5™, Quasar™ 670, LightCycler Red640®, Alexa Fluor 633 Quasar™ 705, LightCycler Red705®, Alexa Fluor® 680, SYTO®9, LC Green®, LC Green® Plus+, EvaGreen™

In an embodiment, the probes carrying the same label differ in melting temperature ($T_m$) in a way that they are distinguishable by melting point on a given instrument, typically harboring a difference in melting temperature of more than 0.1° C., 0.2° C., 0.3° C.1 0.4° C., 0.5° C., 1° C., 1.5° C., 2° C., 2.5° C., 3° C., 4° C., 5° C., 6° C., 7° C., 8° C., 9° C., or 10° C. More than 1° C., 1.5° C., 2° C., 2.5° C., 3° C., 4° C., 5° C. is preferred.

In one embodiment the melting transitions of the double stranded segments can be determined by monitoring fluorescence intensity of double stranded nucleic acid-specific (dsNAS) dyes. In one embodiment, the double stranded nucleic acid-specific dye is selected from the group consisting of SYBR® Green I, SYBR® Gold, ethidium bromide, propidium bomide, Pico Green, Hoechst 33258, YO-PRO-I and YO-YO-I, SYTO®9, LC Green®, LC Green® Plus+, EvaGreen™. These saturation dyes are capable of existing at sufficiently saturating conditions with respect to the DNA during or after amplification, while minimizing the inhibition of PCR. For example, at maximum PCR-compatible concentrations, the dsDNA binding dye has a percent saturation of at least 50%. In other embodiments, the percent saturation is at least 80%. In yet other embodiments, the percent saturation is at least 99%. It is understood that the percent saturation is the percent fluorescence compared to fluorescence of the same dye at saturating concentrations. Saturating concentration is the concentration that provides the highest fluorescence intensity possible in the presence of a predetermined amount of dsDNA. Because these dyes can be present at significantly higher concentrations without significantly interfering with certain nucleic acid reactions, these dyes may be particularly useful for monitoring the conformation of single-stranded nucleic acids and dsDNA.

On advantage of the presently disclosed detection method is that it can be performed simultaneously with the amplification step. This feature permits the full method to be practiced in a "closed tube" format. An exemplary workflow for a closed tube format of the present method is shown at FIG. 1.

Detection probes may be specific for various targets, such as disease markers, pathogens, forensic markers or any other target that may be addressed by means of amplification. The method disclosed herein is particularly suited for the analysis of pathogens. Thus, in embodiment the primers and probes are specific for one or more pathogenic bacteria or viruses.

The most common bacterial disease is tuberculosis, caused by the bacterium *Mycobacterium tuberculosis*, which kills about 2 million people a year, mostly in sub-Saharan Africa. Pathogenic bacteria contribute to other globally important diseases, such as pneumonia, which can be caused by bacteria such as *Streptococcus* and *Pseudomonas*, and foodborne illnesses, which can be caused by bacteria such as *Shigella, Campylobacter* and *Salmonella*.

Pathogenic bacteria also cause infections such as tetanus, typhoid fever, diphtheria, syphilis and leprosy. One of the primary pathways by which food or water become contaminated is from the release of untreated sewage into a drinking water supply or onto cropland, with the result that people who eat or drink contaminated sources become infected. In developing countries most sewage is discharged into the environment or on cropland. This is the typical mode of transmission for the infectious agents of cholera, hepatitis A, polio and rotavirus.

Many respiratory diseases are caused by pathogenic viruses, including Rhinovirus, Parainfluenza Viruses (PIV1-3), Influenza A and Influenza B, Adenovirus B as well as Respiratory Syncytial Virus A and B.

Additionally, several pathogenic bacteria and viruses have been considered for use as biological weapons, including, for example, *Bacillus anthracis, Ebolavirus, Marburgvirus, Yersinia pestis, Vibrio cholerae, F. tularensis, Brucella, Coxiella burnetii, Machupo virus, Coccidioides immitis, Coccidioides posadasii., Burkholderia mallei, Burkholderia pseudomallei, Shigella* ssp. bacterium, *Rickettsia rickettsii, Rickettsia prowazekii, Chlamydophila psittaci,* yellow fever virus, Japanese encephalitis virus, Rift Valley fever virus, Variola major, and Variola minor.

The biowarfare pathogens *B. anthracis* (BA), *Y. pestis* (YP) and *F. tularensis* (FT) have been identified as having the potential to be weapons of mass destruction that could be used to attack both military and civilian populations. These three organisms are especially suitable pathogens for use as biological weapons because they are all highly infectious pathogens and deadly to humans. They can all be delivered in aerosol forms, causing a more deadly pneumonic disease scenario. Clandestine use of antimicrobial-resistant strains or genetic modification of *B. anthracis* to increase virulence or escape vaccine protection is possible. A bioterrorist attack involving pneumonic plague would cause widespread disease and panic, partly due to the communicable nature of the disease. In 1969, the World Health Organization estimated that an aerosol dispersal of 50 kg of virulent *F. tularensis* over a metropolitan area with 5 million inhabitants in a developed country would result in 250,000 illnesses, including 19,000 deaths. An additional threat from the use of these weapons of mass destruction would be the purposeful engineering of antibiotic resistant strains with the intent of foiling diagnostic assays and/or circumventing effective therapeutic stockpiles and treatments. Additionally, there are antibiotic resistant strains of these pathogens arising naturally in areas around the globe which could be isolated and spread by clandestine, low tech, methods.

Therefore, in an embodiment, the target nucleic acid is at least one genomic or plasmid marker specific for pathogens that may be useful as bioweapons. In a further aspect, the target nucleic acid is at least one marker specific for *B. anthracis* (BA), *Y. pestis* (YP), or *F. tularensis* (FT). In another embodiment, the target nucleic acid is at least one ciprofloxacin resistance target. Exemplary targets are set forth in table 1.

In a further embodiment, a detection probe set is provided comprising, consisting, or consisting essentially of: (1) at least one detection probes specific for a ciprofloxacin resistance target selected from the group consisting of gyrA, gyrB-1, gyrB-2, parC, and parE; and (2) at least one detection probes specific for a genomic or plasmid target selected from the group consisting of capB2, capB4, pXO1, pXO2, PLA, PIM, CAF1, tul4, and fopA.

TABLE 1

| Organism | Ciprofloxacin Resistance Targets | Genomic and Plasmid Targets |
|---|---|---|
| *Bacillus anthracis* | gyrA | capB2 |
|  | gyrB-1 | capB4 |
|  | gyrB-2 | pXO1 |
|  | parC | pXO2 |
| *Yersinia pestis* | gyrA | PLA |
|  | pare | PIM |
|  |  | CAF1 |
| *Francisella tularensis* | gyrA | tul4 |
|  |  | fopA |

In a further embodiment, a detection probe set is provided comprising, consisting essentially of, or consisting of at least one detection probes specific for each of gyrA, gyrB-1, gyrB-2, parC, parE, capB2, capB4, pXO1, pXO2, PLA, PIM, CAF1, tul4, and fopA.

As noted above, the amplification step may comprise whole genome amplification, which typically results in amplicons greater than 10 kilobases in length. Normally, probe-based detection requires a much shorter amplicon, typically from 100 to 250 bases in length. Thus, where large amplicons are generated by the amplification step, it may be helpful to fragment the amplicons before detection. Many methods of doing so are known in the art including, without limitation: use of enzymatic methods of fragmenting DNA such as the use of DNase I with $Mn^{2+}$ cofactor (Anderson, S., Nucleic Acids Research, 1981, Vol. 9, No. 13 3015-3027, which is hereby incorporated by reference) and partial digestion using various restriction enzymes (Sambrook, J., Fritsch, E. F., and Maniatis, T., 1989, Molecular Cloning: A laboratory manual, $2^{nd}$ Ed., p. 5.2-5.95, 9.32, Cold Spring Harbor Laboratory Press, New York, which is hereby incorporated by reference); incorporation of random ribonucleoside monophosphate in the amplicon with subsequent alkali digestion; and physical fragmentation, such as by sonication, nebulization, or hydrodynamic shearing. Thus, in an embodiment, the amplified nucleic acids are fragmented before detection.

In one embodiment, uracil residues are incorporated during the amplification reaction. Uracil DNA glycosylase (uracil-N-glycosylase) is the product of the *Escherichia coli* ung-gene, and has been cloned, sequenced and expressed in *E. coli*. Uracil DNA glycosylase (UDG) removes these uracil residues from DNA (single- and double-stranded) without destroying the DNA sugar-phosphodiester backbone, thus preventing its use as a hybridization target or as a template for DNA polymerases. The resulting abasic sites are susceptible to hydrolytic cleavage at elevated temperatures. Thus, removal of uracil bases is usually accompanied by fragmentation of the DNA. The person skilled in the art knows how to use the Uracil DNA glycosylase in order to avoid contamination.

Real-time PCR requires an instrumentation platform that consists of a thermal cycler, a computer, optics for fluorescence excitation and emission collection, and data acquisition and analysis software. These machines, available from several manufacturers, differ in sample capacity (some are 96-well or 384-well standard plate format, others process fewer samples or require specialized glass capillary tubes, some have block format, others a carousel), method of excitation (some use lasers, others broad spectrum light sources with tunable filters or one or more diodes), detection (some use a camera, others a photo multiplier tube, or types of light detection system) and overall sensitivity. There are also platform-specific differences in how the software processes data. In principle the available machines harboring two or more detection channels are suited for the method disclosed herein.

V. Kit

A kit is also disclosed, comprising: (1) at least one hybrid capture component selected from the group consisting of: at least one hybrid capture probe; an anti-DNA-RNA hybrid antibody; and a solid support; and (2) a detection probe set comprising at least four, at least five, or at least six detection probes.

In an embodiment the kit comprises at least four detection probes, wherein at least two detection probes carry the same label.

In another embodiment the kit comprises at least four detection probes, wherein at least three detection probes carry the same label.

In another embodiment the kit comprises at least five detection probes, wherein at least two detection probes carry the same label.

In another embodiment the kit comprises at least five detection probes, wherein at least three detection probes carry the same label.

In another embodiment the kit comprises at least five detection probes, wherein at least four detection probes carry the same label.

In another embodiment the kit comprises at least six detection probes, wherein at least two detection probes carry the same label.

In another embodiment the kit comprises at least six detection probes, wherein at least three detection probes carry the same label.

In another embodiment the kit comprises at least six detection probes, wherein at least four detection probes carry the same label.

In another embodiment the kit comprises at least seven detection probes, wherein at least two detection probes carry the same label.

In another embodiment the kit comprises at least seven detection probes, wherein at least three detection probes carry the same label.

In another embodiment the kit comprises at least seven detection probes, wherein at least four detection probes carry the same label.

In another embodiment the kit comprises at least eight detection probes, wherein at least two detection probes carry the same label In another embodiment the kit comprises at least eight detection probes, wherein at least three detection probes carry the same label.

In another embodiment the kit comprises at least eight probes, wherein at least four probes carry the same label.

In one embodiment, a kit is disclosed comprising at least 6 probes which are able to hybridize, under stringent conditions, to one or more nucleic acid molecules, wherein a) a first group of at least three probes carries a first label and all the probes in this group differ with respect to their melting temperature and b) a second group of at least three probes carries a second label and all the probes in this group differ with respect to their melting temperature.

In another embodiment, a kit is disclosed comprising at least 9 probes which are able to hybridize, under stringent conditions, to one or more nucleic acid molecules, wherein (a) a first group of at least two probes carries a first label and all the probes in this group differ with respect to their melting temperature, (b) a second group of at least two probes carries a second label and (c) a third group of at least two probes carries a third label, and all the probes in this group differ with respect to their melting temperature and at least a third group of at least two probes carries a third label and all the probes in this group differ with respect to their melting temperature.

The probes that differ with respect to their melting temperature (Tm) differ by at least 0.5° C., 1° C., 1.5° C., 2° C., 2.5° C., 3° C., 4° C., 5° C., 6° C., 7° C., 8° C., 9° C., or 10° C. More than 1° C., 1.5° C., 2° C., 2.5° C., 3° C., 4° C., 5° C. is preferred, ideally the probes differ by about 5° C. When used in respect to melting temperatures, the phrase "about" includes all temperatures roundable to the indicated temperature.

Ideally, the probes that have the same label have fixed intervals of difference in melting temperature (Tm), selected in a way that they are reliably distinguishable by melting analysis, for example such as 5° C. In such an embodiment the probes that are, for example, fluorescein labeled would have a melting temperature ($T_m$) of, e.g. 40° C., 45° C., 50° C. and 55° C.

In another embodiment, the kit additionally comprises a buffer, nucleotides and one or enzymes, such as a polymerase. The kit may be adapted as a premix, wherein the user only needs to add the probe.

The kit may used for human or veterinary diagnosis, for testing food or water, for forensic applications, for biodefense applications, or for scientific purposes.

Also provided is a kit for the detection of at least one target nucleic acid in a sample, the kit comprising, consisting of, or consisting essentially of:

i. at least one polynucleotide hybrid capture probe;
ii. an anti-hybrid antibody;
iii. a polymerase;
iv. a detection probe set;
v. optionally, a paramagnetic bead adapted so as to bind the anti-hybrid antibody;
vi. optionally, a denaturation reagent;
vii. optionally, a helicase; and
viii. optionally, a reagent for fragmenting amplified nucleic acids.

In an aspect, a plurality of hybrid capture probes and a plurality of detection probe sets are provided with the kit.

The kit may also include instructions for describing procedures associated with the disclosed methods and assays. The kit may also include a means for transcribing patient information. In an aspect, the means includes paper, a computer, or a device capable of transmitting patient information. The kit can include all the necessary components to complete the methods at the same location where the patient sample is taken.

In an aspect, the kit may include color coded reagents associated with the detection assay. The reagent vials are color coded for ease of use and can be included in a kit. The reagent bottles may also be identified by symbols, letters, or other known identifiers.

As the individual components of the kit come together in an easy to use platform, one advantage of the kit described herein is that it provides for immediate testing of samples. This allows for rapid determination of patient results.

In an aspect, methods of the disclosure can include the collection, processing, and performing the purifying step on patient samples in the field. In one aspect, after the samples are collected, some of the method steps are conducted at the same location where the patient samples are collected. The location may be a village, clinic, laboratory, or communal area where individuals receive medical checkups and evaluations. The location may be permanent or temporary. In an aspect, the nucleic acid is detected at a location, such as a laboratory or clinic, which is different from where the samples are taken. In an aspect, the kit is designed for use in a developing country or geographical areas where access to medical care is not readily available.

This method is further compatible with STM and PC samples.

The following examples are illustrative only and are not intended to limit the disclosure in any way.

EXAMPLES

Figure 2:
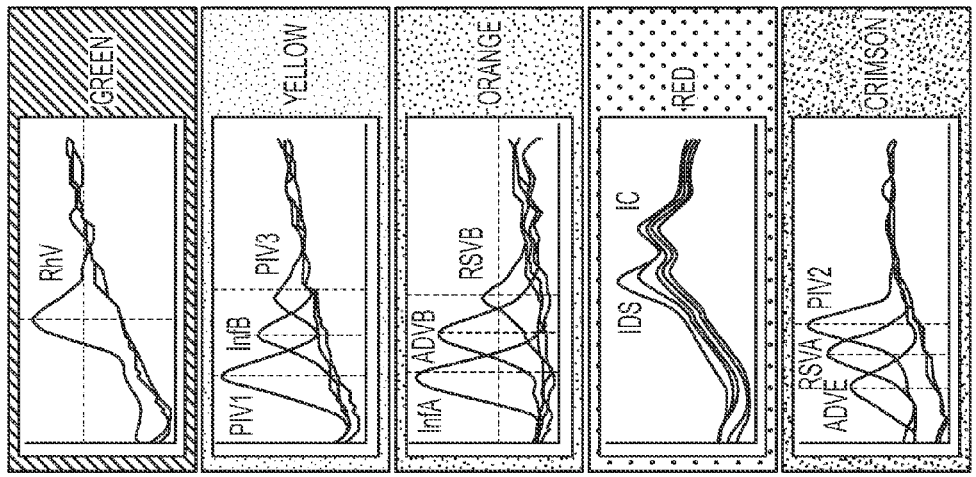
FIG. 2 demonstrates the utility of an exemplary detection probe set in a 12-plex Multiplex PCR to detect viral pathogens such as Rhinovirus, Parainfluenza Viruses (PIV1-3), Influenza A and Influenza B, Adenovirus B as well as Respiratory Syncytial Virus A and B. In addition, two controls are detected, as ID's (human genomic DNA) and IC (plasmid) as shown in Table 2. Clinical Samples were processed on the QIAsymphony® system (Qiagen GmbH, Hilden, Germany) for sample purification. Amplification and detection was performed in the RotorGeneQ™ using the TaqMelt™ principle.
Figure 2:
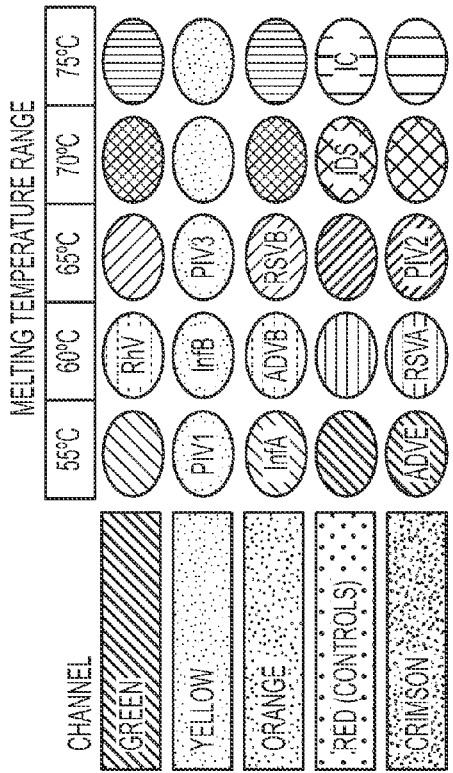
Figure 3:
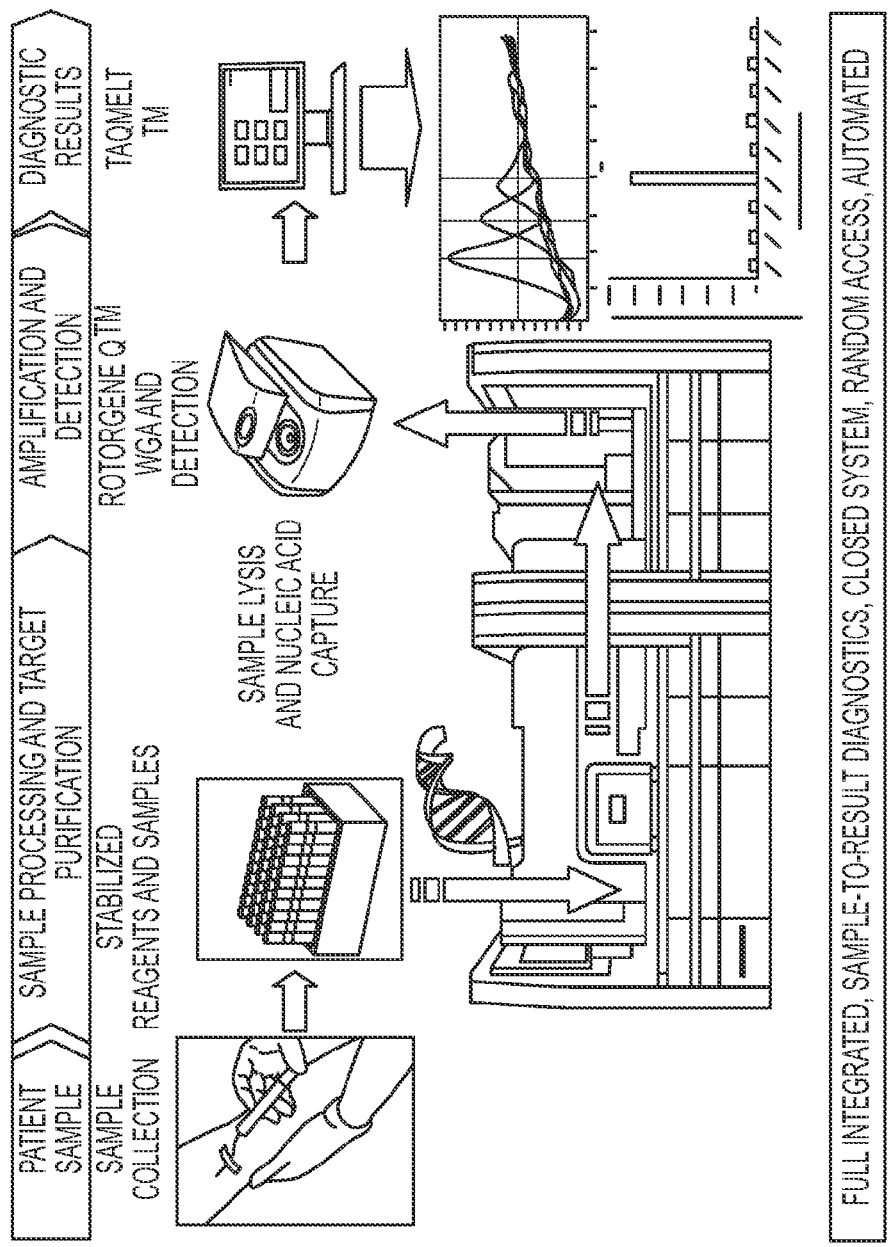
FIG. 3 demonstrates how the presently-disclosed methods could be practiced in a closed tube format using the QIAsymphony® system (Qiagen GmbH, Hilden, Germany).

In this experiment the feasibility of the workflow shown in FIG. 2 is demonstrated. The reactions have been composed as shown in Table 2 and were setup as quadruplicates and carried out with the protocol shown in Table 3.

TABLE 2

Composition of multiplex PCR reaction mix

| Component | Final concentration |
|---|---|
| QuantiFast Multiplex PCR MM 2x | 1x |
| Primer Mix 20x | 1x |
| Probe Mix 50x | 1x |
| RNAse free water | Top up to 25 µl per reaction |
| Final reaction volume | 25 µl |

TABLE 3

PCR Cycling Parameters using QuantiFast™ Multiplex PCR Master Mix

| PCR | | |
|---|---|---|
| Initial PCR activation | 95° C. | 5 min |
| Denaturation | 95° C. | 30 s |
| Annealing/Extension | 60° C. | 30 s |
| Number of cycles | | 40x |
| Melting Curve | | |
| Pre Melt denaturation | 95° C. | 30 s |
| Melting program | | |
| Ramp from | 55° C. 1 | 95° C. Degree Celsius each step |
| Wait for | 90 s | Second of pre-melt conditioning on first step |
| Wait for | 5 s | Second for each step afterwards |

For this purpose the reagents of Table 4 were used.

TABLE 4

Components and material numbers for TaqMelt 6plex PCR setup

| QuantiFast Multiplex PCR Master Mix RNAse free water | Both from: QuantiFast Multiplex PCR Kit, Qiagen, Material-# 204652 |
|---|---|
| GAPDH for GAPDH rev PE-GAPDH-P SRY-for SRY-rev SRY-TM-FAM | Supplier Tib MolBiol http://www.tib-molbiol.de/de/ |

TABLE 4-continued

Components and material numbers for TaqMelt 6plex PCR setup

ALB for
ALB rev
ALB Short(18 bp)_MK
PEc-myc-for
PEc-myc-rev
PEc-mycPro_MK
UBI-TM for
UBI-TM rev
UBI Short(17 bp)_MK
TBP_HE for
TBP_HE rev
TBP_MK Composition of the 20× Primer Mixes and the 50× Probe Mix is indicated in Table 5 and 6, respectively.

TABLE 5

Primer concentrations

| Target | Primer concentration 1x | Primer concentration 20x Primer Mix |
|---|---|---|
| GAPDH | FOR 0.4 µM REV 0.1 µM | FOR 8 µM REV 2 µM |
| SRY | FOR 0.1 µM REV 0.4 µM | FOR 2 µM REV 8 µM |
| ALB | FOR 0.1 µM REV 0.4 µM | FOR 2 µM REV 8 µM |
| cmyc | FOR 0.1 µM REV 0.4 µM | FOR 2 µM REV 8 µM |
| UBI | FOR 0.4 µM REV 0.1 µM | FOR 8 µM REV 2 µM |
| TBP | FOR 0.1 µM REV 0.4 µM | FOR 2 µM REV 8 µM |

TABLE 6

Probe concentrations

| Target | Probe concentration 1x | Probe Mix 50x |
|---|---|---|
| GAPDH (PE-GAPDH-P) | 0.3 µM | 15 µM |
| SRY (SRY-TM-FAM) | 0.3 µM | 15 µM |
| ALB (ALB Short(18 bp)_MK) | 0.8 µM | 40 µM |
| Cmyc (PEc-mycPro_MK) | 0.1 µM | 5 µM |
| UBI (UBI Short(17 bp)_MK) | 0.2 µM | 10 µM |
| TBP (TBP_MK) | 0.2 µM | 10 µM |

Sequences of the primers and probes are shown in Table 7.

TABLE 7

Target Name and Primer/Probe Sequence

| Oligonucleotide Name | Sequence (5'-3') |
|---|---|
| GAPDH for (SEQ ID NO. 1) | TTC CAC CCA TGG CAA AT |
| GAPDH rev (SEQ ID NO. 2) | GAA GAT GGT GAT GGG ATT TC |
| PE-GAPDH-P (SEQ ID NO. 3) | CAA GCT TCC CGT TCT CAG CC |
| SRY-for (SEQ ID NO. 4) | TCC TCA AAA GAA ACC GTG CAT |
| SRY-rev (SEQ ID NO. 5) | AGA TTA ATG GTT GCT AAG GAC TGG AT |
| SRY-TM-FAM (SEQ ID NO. 6) | CAC CAG CAG TAA CTC CCC ACA ACC TCT TT |
| ALB for (SEQ ID NO. 7) | TGC CCT GTG CAG AAG ACT ATC TA |
| ALB rev (SEQ ID NO. 8) | CGA GCT CAA CAA GTG CAG TT |
| ALB Short(18 bp)_MK (SEQ ID NO. 9) | AAG TGA CAG AGT CAC CAA |
| PEc-myc-for (SEQ ID NO. 10) | TCA AGA GGT GCC ACG TCT CC |
| PEc-myc-rev (SEQ ID NO. 11) | TCT TGG CAG CAG GAT AGT CCT T |
| PEc-mycPro_MK (SEQ ID NO. 12) | CAG CAC AAC TAC GCA GCG CCT CC |
| UBI-TM.for (SEQ ID NO. 13) | GTT AAG CTG GCT GTC CTG AAA TAT T |
| UBI-TM.rev (SEQ ID NO. 14) | CCC CAG CAC CAC ATT CAT C |
| UBI Short(17 bp)_MK (SEQ ID NO. 15) | TAG TCG CCT TCG TCG AG |
| TBP_HE for (SEQ ID NO. 16) | TGG AAC CCA CAG TCA TTG ATG A |
| TBP_HE rev (SEQ ID NO. 17) | TGA TCT CCT TGC CAA TGG TGT A |
| TBP_MK (SEQ ID NO. 18) | AGATGCTGCCAATAACTATGCCCGAGG |

As template nucleic acid in PCR, PCR product was generated using cDNA from human leucocytes and the respective for and rev primers for each target shown in Table 7, PCR product was purified using QiaQuick (Qiagen) PCR purification Kit and used at 1:1000 dilution. Templates were added to the individual reactions as given in Table 8:

TABLE 8

Template PCR conditions

| Conditions | Expected Positive Signal (Detection Channel) | Expected Positive Signal (Detection Channel) |
|---|---|---|
| IC only | IC Ubi LC670 (Crimson) | — |
| IC + Target 1 | IC Ubi LC670 (Crimson) | Alb ROX (Orange) |
| IC + Target 2 | IC Ubi LC670 (Crimson) | Cmyc ROX (Orange) |
| IC + Target 3 | IC Ubi LC670 (Crimson) | TBP LC670 (Crimson) |
| IC + Target 4 | IC Ubi LC670 (Crimson) | GAP FAM (Green) |
| IC + Target 5 | IC Ubi LC670 (Crimson) | SRY FAM (Green) |

In the first case "IC-only", only the Ubi template was added, functioning as internal positive control. In the second case, Ubi IC and Target 1 Alb was added. In the third case, Ubi IC and Target 2 Cmyc was used. In the fourth case, Ubi IC and Target 3 TBP was introduced. In the fifth case, Ubi IC and Target 4 GAP was added. For the sixth case, Ubi IC and Target 5 SRY was added as template.

Real-time PCR was performed on a RotorGene 6000 PCR System (6-channel) with a 72 position rotor. Specification of the 6 detection channels are shown in Table 9, including examples of fluorescent dyes suitable to be detected in the respective channels.

TABLE 9

Channel Specifications RotorGene 6000 instrument

| Channel | Excitation source/ Detection filter | Detected Dyes (Examples) |
|---|---|---|
| Blue | 365 ± 20 nm/ 460 ± 15 nm | Edans, Marina Blue ®, AMCA-X, Atto390, Alexa Fluor ®350 |
| Green | 470 ± 10 nm/ 510 ± 5 nm | FAM ™, Fluorescein, Cyan 500 Alexa Fluor ® 488 |
| Yellow | 530 ± 5 nm/ 555 ± 5 nm | JOE ™, VIC ™, HEX ™, TET ™, Yakima Yellow ®, Cal Fluor Orange 560 |
| Orange | 585 ± 5 nm/ 610 ± 5 nm | ROX ™, Cy3.5 ®, Texas Red ®, Alexa Fluor ® 568, CAL Fluor ™ Red 610 |
| Red | 625 ± 10 nm/ 660 ± 10 nm | Cy5 ®, Quasar 670 ™, LightCycler Red 640 ®, Alexa Fluor ™ 633 |
| Crimson | 680 ± 5 nm/ 712 long pass | Quasar705 ™, LC Red 705 ®, LightCycler Red 670 Alexa Fluor ® 680 |

Parameters for PCR cycling and subsequent melting curve are shown in Table 3. Subsequently the run data were analyzed with the appropriate instrument software. $C_T$ values observed in real-time PCR for the internal control (IC) and the respective targets are given in Table 10.

TABLE 10

C_T Results Single Target + Internal Control (IC) Experiment

| Name | Channel | | |
|---|---|---|---|
| | Green | Orange | crimson |
| IC only | | | 21.0 |
| IC + Target 1 | | 22.2 | 21.1 |
| IC + Target 2 | | 17.1 | 21.1 |
| IC + Target 3 | | | 18.2 |
| IC + Target 4 | 16.0 | | 20.7 |
| IC + Target 5 | 16.4 | | 21.0 |

Melting points of the probes (maximum of melting peaks shown in FIG. 8) were determined and results are given in Table 11.

TABLE 11

Tm Results Single Target + Internal Control (IC) Experiment

| Name | Green TM 1 | Orange TM 1 | crimson TM 1 | crimson TM 2 |
|---|---|---|---|---|
| IC only | | | 63.5° C. | |
| IC + Target 1 | | 61.0° C. | 64.0° C. | |
| IC + Target 2 | | 73.8° C. | 64.0° C. | |
| IC + Target 3 | | | 64.3° C. | 70.3° C. |
| IC + Target 4 | 66.0° C. | | 64.0° C. | |
| IC + Target 5 | 72.2° C. | | 64.0° C. | |

Figure 4:
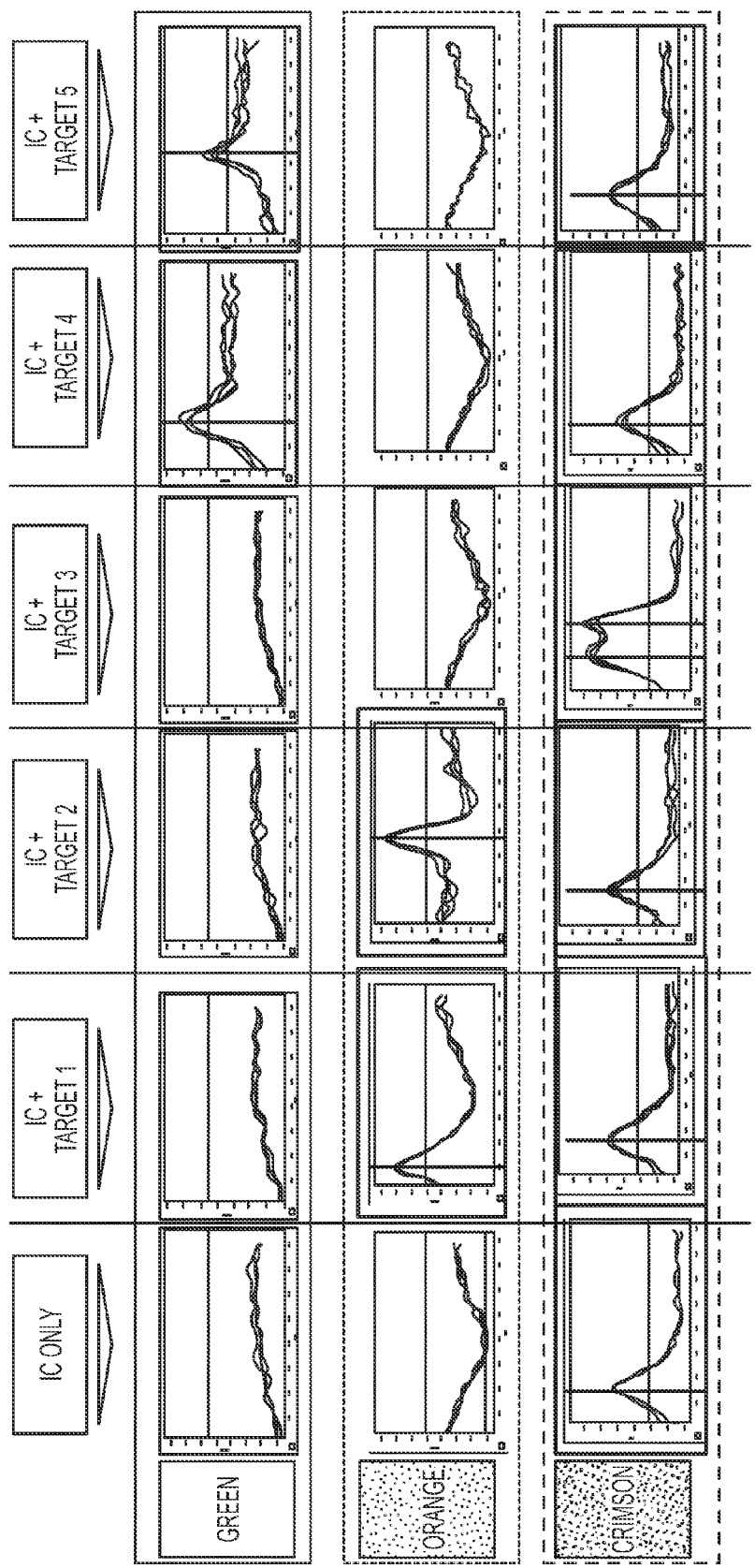
FIG. 4 demonstrates the multiplex capability of the detection step that is presently disclosed.

Observed melting peaks for the 6 different experimental conditions (Table 8) for quadruplicate reactions are shown in FIG. 4. All reactions showed the expected result, showing CT values in the correct detection channel and melting peaks with the expected melting point for respective probe detecting the added target.

What is claimed is:

1. A method of detecting at least one target nucleic acid in a sample, said method comprising:
   (A) generating at least one purified target nucleic acid by:
      (A1) generating at least one double-stranded nucleic acid hybrid by hybridizing the at least one target nucleic acid in the sample to a hybrid probe set comprising at least a first nucleic acid probe specifically hybridized to the at least one target nucleic acid;
      (A2) separating the at least one double-stranded nucleic acid hybrid from the sample, wherein the at least one double-stranded nucleic acid hybrid is the at least one purified target nucleic acid;
   (B) amplifying at least a portion of the at least one purified target nucleic acid, thereby generating at least one amplified nucleic acid; and
   (C) detecting the at least one target nucleic acid by:
      (C1) contacting the at least one amplified nucleic acid with a detection probe set comprising at least three nucleic acid detection probes and forming at least one hybridization complex, wherein:
         (C1(a)) each detection probe of the detection probe set bears a detectable fluorescent label;
         (C1(b)) at least two detection probes of the detection probe set carry the same detectable fluorescent label;
         (C1(c)) each probe carrying the same detectable fluorescent label of the detection probe set has a different melting temperature ($T_m$), and each probe having identical or very similar melting temperatures of the detection probe set carry a different fluorescent label; and
         (C1(d)) each detection probe of the detection probe set hybridizes to a different target nucleic acid sequence;
      (C2) detecting and identifying the detectable fluorescent label of each detection probe of the detection probe set hybridized to the at least one amplified nucleic acid; and
      (C3) detecting the temperature at which each detection probe of the detection probe set dissociates from the at least one amplified nucleic acid;
      wherein the at least one target nucleic acid is detected based on the detectable fluorescent label of each detection probe of the detection probe set and the temperature which each detection probe of the detection probe set dissociates from its corresponding hybridization complex of the at least one hybridization complex.

2. The method of claim 1, wherein the at least one double-stranded nucleic acid hybrid is separated from the sample by binding a hybrid specific molecule to the at least one double-stranded nucleic acid hybrid.

3. The method of claim 2, wherein said binding of the hybrid specific molecule to the at least one double-stranded nucleic acid hybrid immobilizes the at least one purified target nucleic acid to a solid phase.

4. The method of claim 3, wherein the hybrid specific molecule is bound to or adapted to be bound to the solid phrase, wherein the solid phrase is a solid support.

5. The method of claim 3, wherein said amplifying at least a portion of the at least one purified target nucleic acid is performed after the at least one purified target nucleic acid is immobilized to the solid phase.

6. The method of claim 2, wherein the double-stranded nucleic acid hybrid is a DNA:RNA hybrid and the hybrid specific molecule is an anti-DNA:RNA hybrid antibody or a fragment thereof.

7. The method of claim 1, wherein said amplifying at least a portion of the at least one purified target nucleic acid is performed by an isothermal amplification.

8. The method of claim 7, wherein the isothermal amplification utilizes: (a) a polymerase having strand displacement activity; and (b) random primers.

9. The method of claim 8, wherein the at least one target nucleic acid comprises a whole genome and the isothermal amplification is a whole genome amplification.

10. The method of claim 1, wherein the melting temperatures of all probes carrying the same detectable fluorescent label of the detection probe set differ at least 0.1° C.

11. The method of claim 1, wherein the melting temperatures of all probes carrying the same detectable fluorescent label of the detection probe set differ 0.5° C. to 10° C.

12. The method of claim 1, wherein the melting temperatures of all probes of the detection probe set differ about 5° C.

13. The method of claim 1, wherein the detectable fluorescent label comprises at least one fluorophore selected from the group consisting of:
   c1(d): a fluorophore capable of being excited by an excitation source at 365±20 nm and detected using a 460±15 nm detection filter;
   c1(e): a fluorophore capable of being excited by an excitation source at 470±10 nm and detected using a 510±5 nm detection filter;
   c1(f): a fluorophore capable of being excited by an excitation source at 530±5 nm and detected using a 555±5 nm detection filter;
   c1(g): a fluorophore capable of being excited by an excitation source at 585±5 nm and detected using a 610±5 nm detection filter;
   c1(h): a fluorophore capable of being excited by an excitation source at 625±10 nm and detected using a of 660±10 nm detection filter; and
   c1(i): a fluorophore capable of being excited by an excitation source at 680±5 nm and detected using a 712 nm long pass detection filter.

14. The method of claim 13, wherein the detection probe set comprises at least three groups of probes, wherein each probe of said at least three groups
   comprises a fluorophore selected from the group consisting of c1 (d) to c1 (i); and
   one probe of said at least three groups has a melting temperature at least 0.1° C. different from other probes of the same group of said at least three groups.

15. The method of claim 1, wherein the detection probe set comprises:
c1(d): at least one detection probe specific for a ciprofloxacin resistance target selected from the group consisting of gyrA, gyrB-1, gyrB-2, parC, and parE; and
c1(e): at least one detection probe specific for a genomic or plasmid target selected from the group consisting of capB2, capB4, pXO1, pXO2, PLA, PIM, CAF1, tul4, and fopA.

16. The method of claim 1, wherein the detection probe set comprises at least one detection probe specific for a nucleic acid derived from a pathogen selected from the group consisting of: *Mycobacterium tuberculosis, Streptococcus, Pseudomonas, Shigella, Campylobacter, Salmonella*, Respiratory Syncytial Virus A, Respiratory Syncytial Virus B; adenovirus, herpes simplex virus (HSV) 1, HSV2, Influenza A/B, hMPV Parainfluenzavirus 1-4, Coronavirus, Rhinovirus, Enterovirus, Bocavirus, cytomegalovirus (CMV), human immunodeficiency virus, influenza A virus subtype H1N1, *chlamydia, Neisseria gonorrhoeae, Trichomonas vaginalis, Staphylococcus aureus*, SARS-associated coronavirus, *Escherichia coli, Bacillus anthracis*, Ebolavirus, Marburgvirus, *Yersinia pestis, Vibrio cholerae, F. tularensis, Brucella, Coxiella burnetii*, Machupo virus, *Coccidioides immitis, Coccidioides posadasii., Burkholderia mallei, Burkholderia pseudomallei, Shigella* ssp. bacterium, *Rickettsia rickettsii, Rickettsia prowazekii, Chlamydophila psittaci*, yellow fever virus, Japanese encephalitis virus, Rift Valley fever virus, *Variola major*, and *Variola minor*.

17. The method of claim 1, wherein the amplifying and detecting steps are performed simultaneously.

18. The method of claim 1, wherein step (C3) further comprises determining the temperature which each detection probe of the detection probe set dissociates from its corresponding hybridization complex of the at least one hybridization complex which includes contacting the at least one amplified nucleic acid with a double stranded nucleic acid-specific dye.

19. The method of claim 18, wherein the double stranded nucleic acid-specific dye is selected from the group consisting of SYBR® Green I, SYBR® Gold, ethidium bromide, propidium iodide, Pico Green, Hoechst 33258, YO-PRO-I and YO-YO-I, SYTO®9, LC Green®, LC Green® Plus+, and EvaGreen ™.

20. A detection probe set comprising at least five nucleic acid probes specific for different target nucleic acids, each of the at least five nucleic acid probes comprising a detectable label, wherein:

(A) at least two of the nucleic acid probes of the at least five nucleic acid probes comprise the same detectable label;
(B) each probe carrying the same detectable label of the nucleic acid probes of the at least five nucleic acid probes has a different melting temperature; and
(C) the detectable label is a fluorophore selected from the group consisting of:
(C1): a fluorophore capable of being excited by an excitation source at 365±20 nm and detected using a 460±15 nm detection filter;
(C2): a fluorophore capable of being excited by an excitation source at 470±10 nm and detected using a 510±5 nm detection filter;
(C3): a fluorophore capable of being excited by an excitation source at 530±5 nm and detected using a 555±5 nm detection filter;
(C4): a fluorophore capable of being excited by an excitation source at 585±5 nm and detected using a 610±5 nm detection filter;
(C5): a fluorophore capable of being excited by an excitation source at 625±10 nm and detected using a of 660±10 nm detection filter; and
(C6): a fluorophore capable of being excited by an excitation source at 680±5 nm and detected using a 712 nm long pass detection filter.

21. The detection probe set of claim 20, wherein the melting temperature of each of the at least five nucleic acid probes differs at least 0.1° C.

22. The detection probe set of claim 20, wherein the melting temperature of each of the at least five nucleic acid probes differs 0.5° C. to 10° C.

23. The detection probe set of claim 20, wherein the melting temperature of each of the at least five nucleic acid probes differs about 5° C.

24. A kit for detecting a target nucleic acid comprising:
(A) at least one hybrid capture probe;
(B) the detection probe set of claim 20; and optionally comprising one or more of the following:
(C) a polymerase;
(D) a double stranded nucleic acid-specific dye;
(E) an anti-DNA-RNA hybrid antibody;
(F) a solid support capable of binding to the anti-hybrid antibody;
(G) a denaturation reagent;
(H) a helicase; and
(I) a reagent for fragmenting an amplified nucleic acid.

* * * * *

```
                        SEQUENCE LISTING

<160> NUMBER OF SEQ ID NOS: 18

<210> SEQ ID NO 1
<211> LENGTH: 17
<212> TYPE: DNA
<213> ORGANISM: Artificial Sequence
<220> FEATURE:
<223> OTHER INFORMATION: Primer

<400> SEQUENCE: 1
ttccacccat ggcaaat                                                       17

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
gaagatggtg atgggatttc                                                    20

<210> SEQ ID NO 3
<211> LENGTH: 20
<212> TYPE: DNA
<213> ORGANISM: Artificial Sequence
<220> FEATURE:
<223> OTHER INFORMATION: Probe

<400> SEQUENCE: 3
caagcttccc gttctcagcc                                                    20

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
tcctcaaaag aaaccgtgca t                                                  21

<210> SEQ ID NO 5
<211> LENGTH: 26
<212> TYPE: DNA
<213> ORGANISM: Artificial Sequence
```

```
<220> FEATURE:
<223> OTHER INFORMATION: Primer

<400> SEQUENCE: 5
agattaatgg ttgctaagga ctggat                                      26

<210> SEQ ID NO 6
<211> LENGTH: 29
<212> TYPE: DNA
<213> ORGANISM: Artificial Sequence
<220> FEATURE:
<223> OTHER INFORMATION: Probe

<400> SEQUENCE: 6
caccagcagt aactccccac aacctcttt                                   29

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
tgccctgtgc agaagactat cta                                         23

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
cgagctcaac aagtgcagtt                                             20

<210> SEQ ID NO 9
<211> LENGTH: 18
<212> TYPE: DNA
<213> ORGANISM: Artificial Sequence
<220> FEATURE:
<223> OTHER INFORMATION: Probe

<400> SEQUENCE: 9
aagtgacaga gtcaccaa                                               18

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tcaagaggtg ccacgtctcc                                             20

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
tcttggcagc aggatagtcc tt                                          22
```

<210> SEQ ID NO 12
<211> LENGTH: 23
<212> TYPE: DNA
<213> ORGANISM: Artificial Sequence
<220> FEATURE:
<223> OTHER INFORMATION: Probe

<400> SEQUENCE: 12
cagcacaact acgcagcgcc tcc                                          23

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
gttaagctgg ctgtcctgaa atatt                                        25

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
ccccagcacc acattcatc                                               19

<210> SEQ ID NO 15
<211> LENGTH: 17
<212> TYPE: DNA
<213> ORGANISM: Artificial Sequence
<220> FEATURE:
<223> OTHER INFORMATION: Probe

<400> SEQUENCE: 15
tagtcgcctt cgtcgag                                                 17

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
tggaacccac agtcattgat ga                                           22

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
tgatctcctt gccaatggtg ta                                           22

<210> SEQ ID NO 18
<211> LENGTH: 27
<212> TYPE: DNA
<213> ORGANISM: Artificial Sequence
<220> FEATURE:
<223> OTHER INFORMATION: Probe

```
<400> SEQUENCE: 18
agatgctgcc aataactatg cccgagg                                                27
```